(12) United States Patent
Meirav et al.

(10) Patent No.: US 9,976,760 B2
(45) Date of Patent: *May 22, 2018

(54) METHOD AND SYSTEM FOR CONDITIONING AIR IN AN ENCLOSED ENVIRONMENT WITH DISTRIBUTED AIR CIRCULATION SYSTEMS

(71) Applicant: ENVERID SYSTEMS, INC., Needham, MA (US)

(72) Inventors: Udi Meirav, Newton, MA (US); Israel Biran, Avihayil (IL); Abraham Bechar, Tel-Aviv (IL); Asael Meruham, Beit-Dagan (IL)

(73) Assignee: ENVERID SYSTEMS, INC., Needham, MA (US)

( * ) Notice: Subject to any disclaimer, the term of this patent is extended or adjusted under 35 U.S.C. 154(b) by 68 days.

This patent is subject to a terminal disclaimer.

(21) Appl. No.: 15/064,584

(22) Filed: Mar. 8, 2016

(65) Prior Publication Data

US 2016/0187012 A1    Jun. 30, 2016

Related U.S. Application Data

(63) Continuation of application No. 14/359,280, filed as application No. PCT/US2012/065600 on Nov. 16, 2012, now Pat. No. 9,316,410.

(Continued)

(51) Int. Cl.
*B01D 53/02* (2006.01)
*F24F 3/16* (2006.01)
(Continued)

(52) U.S. Cl.
CPC .............. *F24F 3/1603* (2013.01); *A61L 9/22* (2013.01); *B01D 53/0446* (2013.01);
(Continued)

(58) Field of Classification Search
CPC ................... A61L 2209/16; A61L 9/22; F24F 2003/1614; F24F 2003/1621;
(Continued)

(56) References Cited

U.S. PATENT DOCUMENTS

| 1,522,480 A | 1/1925 | Allen |
| 1,836,301 A | 12/1931 | Bechtold |

(Continued)

FOREIGN PATENT DOCUMENTS

| CA | 2640152 A1 | 4/2010 |
| CN | 2141873 Y | 9/1993 |

(Continued)

OTHER PUBLICATIONS

"EPA Ventilation and Air Quality in Offices, Fact Sheet" United States Environmental Protection Agency, Air and Radiation (6609J), Revised Jul. 1990.

(Continued)

*Primary Examiner* — Christopher P Jones
(74) *Attorney, Agent, or Firm* — Cooley LLP

(57) ABSTRACT

A system for conditioning air in a building including a fan-coil unit arranged adjacent to or within an indoor space within the building and additionally configured to at least one of heat and cool the air of the indoor space, and a scrubber arranged adjacent to or within the indoor space, the scrubber configured during a scrub cycle for scrubbing of indoor air from the indoor space. The scrubber includes one or more adsorbent materials arranged therein to adsorb at least one predetermined gas from the indoor air during the scrub cycle, a source of outdoor air, and an exhaust, wherein the scrubber is configured during a purge cycle to direct a purging air flow received from the source of outdoor air over and/or through the adsorbent materials to purge at least a portion of the at least one predetermined gas adsorbed by the (Continued)

adsorbent materials during the scrub cycle from the adsorbent materials and thereafter exhausting the flow via the exhaust.

19 Claims, 19 Drawing Sheets

Related U.S. Application Data

(60) Provisional application No. 61/560,824, filed on Nov. 17, 2011, provisional application No. 61/560,827, filed on Nov. 17, 2011, provisional application No. 61/704,850, filed on Sep. 24, 2012.

(51) Int. Cl.

| | |
|---|---|
| A61L 9/22 | (2006.01) |
| F24F 3/06 | (2006.01) |
| F24H 3/06 | (2006.01) |
| F24H 3/12 | (2006.01) |
| F28D 1/04 | (2006.01) |
| B01D 53/04 | (2006.01) |
| F24F 1/00 | (2011.01) |
| F24F 11/00 | (2018.01) |

(52) U.S. Cl.
CPC ............ *F24F 1/0007* (2013.01); *F24F 3/06* (2013.01); *F24F 3/166* (2013.01); *F24F 11/001* (2013.01); *F24F 11/0017* (2013.01); *F24F 11/0034* (2013.01); *F24H 3/06* (2013.01); *F24H 3/062* (2013.01); *F24H 3/12* (2013.01); *F28D 1/04* (2013.01); *A61L 2209/16* (2013.01); *B01D 2257/11* (2013.01); *B01D 2257/302* (2013.01); *B01D 2257/404* (2013.01); *B01D 2257/502* (2013.01); *B01D 2257/504* (2013.01); *B01D 2257/708* (2013.01); *B01D 2259/40086* (2013.01); *B01D 2259/4508* (2013.01); *F24F 2003/1614* (2013.01); *F24F 2003/1621* (2013.01); *F24F 2003/1664* (2013.01); *F24F 2003/1671* (2013.01); *F24F 2011/0057* (2013.01)

(58) Field of Classification Search
CPC ....... F24F 2003/1664; F24F 2003/1671; F24F 3/06; F24F 3/1603; F24F 3/166; F24H 3/06; F24H 3/062; F24H 3/12; F28D 1/04
See application file for complete search history.

(56) References Cited

U.S. PATENT DOCUMENTS

| | | |
|---|---|---|
| 3,107,641 A | 10/1963 | Haynes |
| 3,511,595 A | 5/1970 | Fuchs |
| 3,619,130 A | 11/1971 | Ventriglio et al. |
| 3,702,049 A | 11/1972 | Morris, Jr. |
| 3,751,848 A | 8/1973 | Ahlstrand |
| 3,808,773 A | 5/1974 | Reyhing et al. |
| 3,885,928 A | 5/1975 | Wu |
| 4,182,743 A | 1/1980 | Rainer et al. |
| 4,228,197 A | 10/1980 | Means |
| 4,249,915 A | 2/1981 | Sircar et al. |
| 4,322,394 A | 3/1982 | Mezey et al. |
| 4,325,921 A | 4/1982 | Aiken et al. |
| 4,433,981 A | 2/1984 | Slaugh et al. |
| 4,451,435 A | 5/1984 | Holter et al. |
| 4,530,817 A | 7/1985 | Hölter et al. |
| 4,551,304 A | 11/1985 | Holter et al. |
| 4,559,066 A | 12/1985 | Hunter et al. |
| 4,711,645 A | 12/1987 | Kumar |
| 4,810,266 A | 3/1989 | Zinnen et al. |
| 4,892,719 A | 1/1990 | Gesser |
| 4,917,862 A | 4/1990 | Kraw et al. |
| 4,987,952 A | 1/1991 | Beal et al. |
| 5,046,319 A | 9/1991 | Jones |
| 5,087,597 A | 2/1992 | Leal et al. |
| 5,137,548 A | 8/1992 | Grenier et al. |
| 5,186,903 A | 2/1993 | Cornwell |
| 5,221,520 A | 6/1993 | Cornwell |
| 5,231,063 A | 7/1993 | Fukumoto et al. |
| 5,281,254 A | 1/1994 | Birbara et al. |
| 5,290,345 A | 3/1994 | Osendorf et al. |
| 5,292,280 A | 3/1994 | Janu et al. |
| 5,322,473 A | 6/1994 | Hofstra et al. |
| 5,376,614 A | 12/1994 | Birbara et al. |
| 5,389,120 A | 2/1995 | Sewell et al. |
| 5,464,369 A | 11/1995 | Federspiel |
| 5,492,683 A | 2/1996 | Birbara et al. |
| 5,584,916 A | 12/1996 | Yamashita et al. |
| 5,675,979 A | 10/1997 | Shah |
| 5,707,005 A | 1/1998 | Kettler et al. |
| 5,827,355 A | 10/1998 | Wilson |
| 5,869,323 A | 2/1999 | Horn |
| 5,876,488 A | 3/1999 | Birbara et al. |
| 5,948,355 A | 9/1999 | Fujishima et al. |
| 5,964,927 A | 10/1999 | Graham et al. |
| 5,984,198 A | 11/1999 | Bennett et al. |
| 6,027,550 A | 2/2000 | Vickery |
| 6,102,793 A | 8/2000 | Hansen |
| 6,113,674 A | 9/2000 | Graham et al. |
| 6,123,617 A | 9/2000 | Johnson |
| 6,187,596 B1 | 2/2001 | Dallas et al. |
| 6,280,691 B1 | 8/2001 | Homeyer et al. |
| 6,364,938 B1 | 4/2002 | Birbara et al. |
| 6,432,367 B1 | 8/2002 | Munk |
| 6,533,847 B2 | 3/2003 | Seguin et al. |
| 6,547,854 B1 | 4/2003 | Gray et al. |
| 6,605,132 B2 | 8/2003 | Fielding |
| 6,623,550 B2 | 9/2003 | Shah |
| 6,711,470 B1 | 3/2004 | Hartenstein et al. |
| 6,726,558 B1 | 4/2004 | Meirav |
| 6,773,477 B2 | 8/2004 | Lindsay |
| 6,797,246 B2 | 9/2004 | Hopkins |
| 6,866,701 B2 | 3/2005 | Meirav |
| 6,908,497 B1 | 6/2005 | Sirwardane |
| 6,916,239 B2 | 7/2005 | Siddaramanna et al. |
| 6,916,360 B2 | 7/2005 | Seguin et al. |
| 6,930,193 B2 | 8/2005 | Yaghi et al. |
| 6,974,496 B2 | 12/2005 | Wegeng et al. |
| 7,288,136 B1 | 10/2007 | Gray et al. |
| 7,407,633 B2 | 8/2008 | Potember et al. |
| 7,449,053 B2 | 11/2008 | Hallam |
| 7,472,554 B2 | 1/2009 | Vosburgh |
| 7,645,323 B2 | 1/2010 | Massenbauer-Strafe et al. |
| 7,662,746 B2 | 2/2010 | Yaghi et al. |
| 7,666,077 B1 | 2/2010 | Thelen |
| 7,802,443 B2 | 9/2010 | Wetzel |
| 7,891,573 B2 | 2/2011 | Finkam et al. |
| 8,157,892 B2 | 4/2012 | Meirav |
| 8,317,890 B2 | 11/2012 | Raether et al. |
| 8,491,710 B2 | 7/2013 | Meirav |
| 2001/0021363 A1 | 9/2001 | Poles et al. |
| 2002/0056373 A1 | 5/2002 | Fielding |
| 2002/0078828 A1 | 6/2002 | Kishkovich et al. |
| 2002/0083833 A1 | 7/2002 | Nalette et al. |
| 2002/0147109 A1 | 10/2002 | Branover et al. |
| 2002/0183201 A1 | 12/2002 | Barnwell et al. |
| 2002/0193064 A1 | 12/2002 | Michalakos et al. |
| 2003/0097086 A1 | 5/2003 | Gura |
| 2003/0188745 A1 | 10/2003 | Deas et al. |
| 2004/0005252 A1 | 1/2004 | Siess |
| 2004/0069144 A1 | 4/2004 | Wegeng et al. |
| 2004/0118287 A1 | 6/2004 | Jaffe et al. |
| 2005/0191219 A1 | 9/2005 | Uslenghi et al. |
| 2005/0262869 A1 | 12/2005 | Tongu et al. |
| 2005/0284291 A1 | 12/2005 | Alizadeh-Khiavi et al. |
| 2006/0032241 A1 | 2/2006 | Gontcharov et al. |
| 2006/0054023 A1 | 3/2006 | Raetz et al. |
| 2006/0079172 A1 | 4/2006 | Fleming et al. |
| 2006/0148642 A1 | 7/2006 | Ryu et al. |
| 2006/0249019 A1 | 11/2006 | Roychoudhury et al. |

(56) References Cited

U.S. PATENT DOCUMENTS

| | | |
|---|---|---|
| 2008/0119356 A1 | 3/2008 | Ryu et al. |
| 2008/0078289 A1 | 4/2008 | Sergi et al. |
| 2008/0127821 A1 | 6/2008 | Noack et al. |
| 2008/0135060 A1 | 6/2008 | Kuo et al. |
| 2008/0182506 A1 | 7/2008 | Jackson et al. |
| 2008/0293976 A1 | 11/2008 | Olah et al. |
| 2009/0000621 A1 | 1/2009 | Haggblom et al. |
| 2009/0120288 A1 | 5/2009 | Lackner et al. |
| 2009/0220388 A1 | 9/2009 | Monzyk et al. |
| 2009/0260372 A1 | 10/2009 | Skinner et al. |
| 2010/0076605 A1 | 3/2010 | Harrod et al. |
| 2010/0154636 A1 | 6/2010 | Liu et al. |
| 2010/0254868 A1 | 10/2010 | Obee et al. |
| 2010/0262298 A1 | 10/2010 | Johnson et al. |
| 2010/0278711 A1 | 11/2010 | Find |
| 2011/0064607 A1 | 3/2011 | Hedman |
| 2011/0079143 A1 | 4/2011 | Marotta et al. |
| 2011/0085933 A1 | 4/2011 | Mazyek et al. |
| 2011/0146494 A1 | 6/2011 | Desai et al. |
| 2011/0179948 A1 | 7/2011 | Choi et al. |
| 2011/0189075 A1 | 8/2011 | Wright et al. |
| 2011/0192172 A1 | 8/2011 | Delacruz |
| 2011/0198055 A1 | 8/2011 | Meirav et al. |
| 2011/0206572 A1 | 8/2011 | McKenna et al. |
| 2011/0250121 A1 | 10/2011 | Schmidt |
| 2011/0262327 A1 | 10/2011 | Dillon et al. |
| 2011/0265648 A1 | 11/2011 | Meirav |
| 2011/0269919 A1 | 11/2011 | Min et al. |
| 2011/0277490 A1 | 11/2011 | Meirav |
| 2011/0296872 A1 | 12/2011 | Eisenberger |
| 2012/0004092 A1 | 1/2012 | Raatschen et al. |
| 2012/0012005 A1 | 1/2012 | Burke |
| 2012/0052786 A1 | 3/2012 | Clawsey |
| 2012/0148858 A1 | 6/2012 | Wu |
| 2012/0168113 A1 | 7/2012 | Karamanos |
| 2012/0216676 A1 | 8/2012 | Addiego et al. |
| 2012/0222500 A1 | 9/2012 | Riess et al. |
| 2013/0052113 A1 | 2/2013 | Molins et al. |

FOREIGN PATENT DOCUMENTS

| | | |
|---|---|---|
| CN | 101500704 A | 8/2009 |
| CN | 201363833 Y | 12/2009 |
| EP | 0 475493 A2 | 3/1992 |
| ES | 2387791 A1 | 4/1983 |
| JP | 56-158126 A | 12/1981 |
| JP | 59-225232 A | 12/1984 |
| JP | 60194243 | 10/1985 |
| JP | 02-092373 A | 3/1990 |
| JP | 09085043 A | 3/1997 |
| JP | 2001-170435 A | 6/2001 |
| JP | 2001232127 A | 8/2001 |
| JP | 3207936 B2 | 9/2001 |
| JP | 2005-090941 A | 4/2005 |
| JP | 2006275487 A | 10/2006 |
| JP | 2009-202137 A | 9/2009 |
| JP | 2010-149086 A | 7/2010 |
| WO | WO 198805693 A1 | 8/1988 |
| WO | WO-1998805693 | 8/1988 |
| WO | WO-2002008160 A1 | 1/2002 |
| WO | WO-200212796 A2 | 2/2002 |
| WO | WO-2007128584 A1 | 11/2007 |
| WO | WO-2007128584 A1 | 11/2007 |
| WO | WO 2008155543 A2 | 12/2008 |
| WO | WO 2009126607 A2 | 10/2009 |
| WO | WO 2010091831 A1 | 8/2010 |
| WO | WO 2010124388 A1 | 11/2010 |
| WO | WO 2011114168 A1 | 9/2011 |
| WO | WO 2011146478 A1 | 11/2011 |
| WO | WO 2012134415 A1 | 10/2012 |
| WO | WO 2012158911 A2 | 11/2012 |
| WO | WO 2013074973 A1 | 5/2013 |
| WO | WO 2013106573 A1 | 7/2013 |

OTHER PUBLICATIONS

International Search Report and The Written Opinion of the International Searching Authority for International Application No. PCT/US2011/036801 dated Sep. 27, 2011.

International Preliminary Report on Patentability, dated Nov. 29, 2012, for PCT/US2011/036801.

International Search Report and The Written Opinion of the International Searching Authority for International Application No. PCT/US2012/024333 dated Sep. 5, 2012.

International Search Report dated Jul. 25, 2013 for International Application No. PCT/US2013/035933, filed Apr. 10, 2013.

International Search Report of PCT/US2012/038343, dated Jan. 28, 2013.

Gesser, H.D., "The Reduction of Indoor Formaldehyde Gas and that Emanating from Urea Formaldehyde Foam Insulation (UFFI)", Environmental International, vol. 10, pp. 305-308, 1984.

Jones, Christopher W., "CO2 Capture from Dilute Gases as a Component of Modern Global Carbon Management", Annual Review of Chemical and Biomolecular Engineering, vol. 2, pp. 31-52, 2011.

Ma, Chanjuan et al., "Removal of low-concentration formaldehyde in air by adsorption on activated carbon modified by hexamethylene diamine", Carbon, vol. 49, pp. 2869-2877, 2011.

Nuckols, M. L. et al., "Technical Manual: Design Guidelines For Carbon Dioxide Scrubbers", Naval Coastal Systems Center, vol. 4110, pp. 1-83, Revision A, Jul. 1985.

United States Environmental Protection Agency, "Carbon Adsorption for Control of VOC Emissions: Theory and Full Scale System Performance", vol. 450, pp. 88-012, Jun. 1988.

Serna-Guerrero, Rodrigo et al., "Triamine-grafted pore-expanded mesoporous silica for CO2 capture: Effect of moisture and adsorbent regeneration strategies", Adsorption, vol. 16, pp. 567-575, 2010.

International Search Report and Written Opinion, dated Dec. 20, 2013 for PCT/US2013/051077.

International Search Report and Written Opinion, dated Jan. 3, 2014 for PCT/US2013/042239.

International Search Report and Written Opinion, dated Mar. 22, 2013 for PCT/US2012/065600.

International Search Report and Written Opinion, dated Mar. 29, 2013 for PCT/US2013/021033.

International Search Report and Written Opinion, dated Mar. 17, 2014 for PCT/US2013/070383.

International Search Report and Written Opinion, dated Jul. 10, 2014 for PCT/US2014/023488.

International Search Report and Written Opinion, dated Aug. 15, 2014 for PCT/US2014/031009.

International Search Report and Written Opinion, dated Nov. 24, 2014 for PCT/US2014/055863.

International Search Report and Written Opinion, dated Nov. 24, 2014 for PCT/US2014/056097.

Sidheswaran, Meera A. et al., "Energy efficient indoor VOC air cleaning with activated carbon filter (ACF) filters", Building and Environment, vol. 47, Apr. 2011, pp. 357-367.

Zorflex® ACC, 100% Activated Woven Carbon Cloth, Calgon Carbon Corporation, 2008, www.calgoncarbon.com, 2 pages.

Zorflex® ACC, 100% Activated Woven Carbon Cloth, Calgon Carbon Corporation, 2011, www.calgoncarbon.com, 2 pages.

Gray, M. L. et al., "Performance of immobilized tertiary amine solid sorbents for the capture of carbon dioxide", International Journal of Greenhouse Gas Control, vol. 2, Issue 1, Jan. 2008, pp. 3-8.

International Preliminary Report on Patentability, dated Aug. 22, 2013, for PCT/US2012/024333.

International Preliminary Report on Patentability, dated Nov. 28, 2013 for PCT/US2012/038343.

International Preliminary Report on Patentability, dated May 30, 2014 for PCT/US2012/065600.

International Preliminary Report on Patentability, dated Jul. 24, 2014 for PCT/US2013/021033.

International Preliminary Report on Patentability, dated Dec. 4, 2014 for PCT/US2013/042239.

(56) References Cited

OTHER PUBLICATIONS

International Preliminary Report on Patentability, dated Jan. 29, 2015 for PCT/US2013/051077.
International Search Report and Written Opinion, dated Dec. 19, 2013 for PCT/US2013/061422.
International Preliminary Report on Patentability, dated Apr. 2, 2015 for PCT/US2013/061422.
International Preliminary Report on Patentability, dated May 28, 2015 for PCT/US2013/070383.
International Search Report and Written Opinion, dated Sep. 2, 2014, for PCT/US2014/035114.
International Search Report and Written Opinion, dated May 15, 2015, for PCT/US2015/015690.
Goeppert et al., "Carbon Dioxide Capture from the Air Using a Polyamine Based Regenerable Solid Adsorbent," J. Am. Chem. Soc., vol. 133, No. 50, Nov. 21, 2011 (Nov. 21, 2011) pp. 20164-20167 entire document.
International Search Report and Written Opinion, dated May 5, 2014, for PCT/US2014/011078.

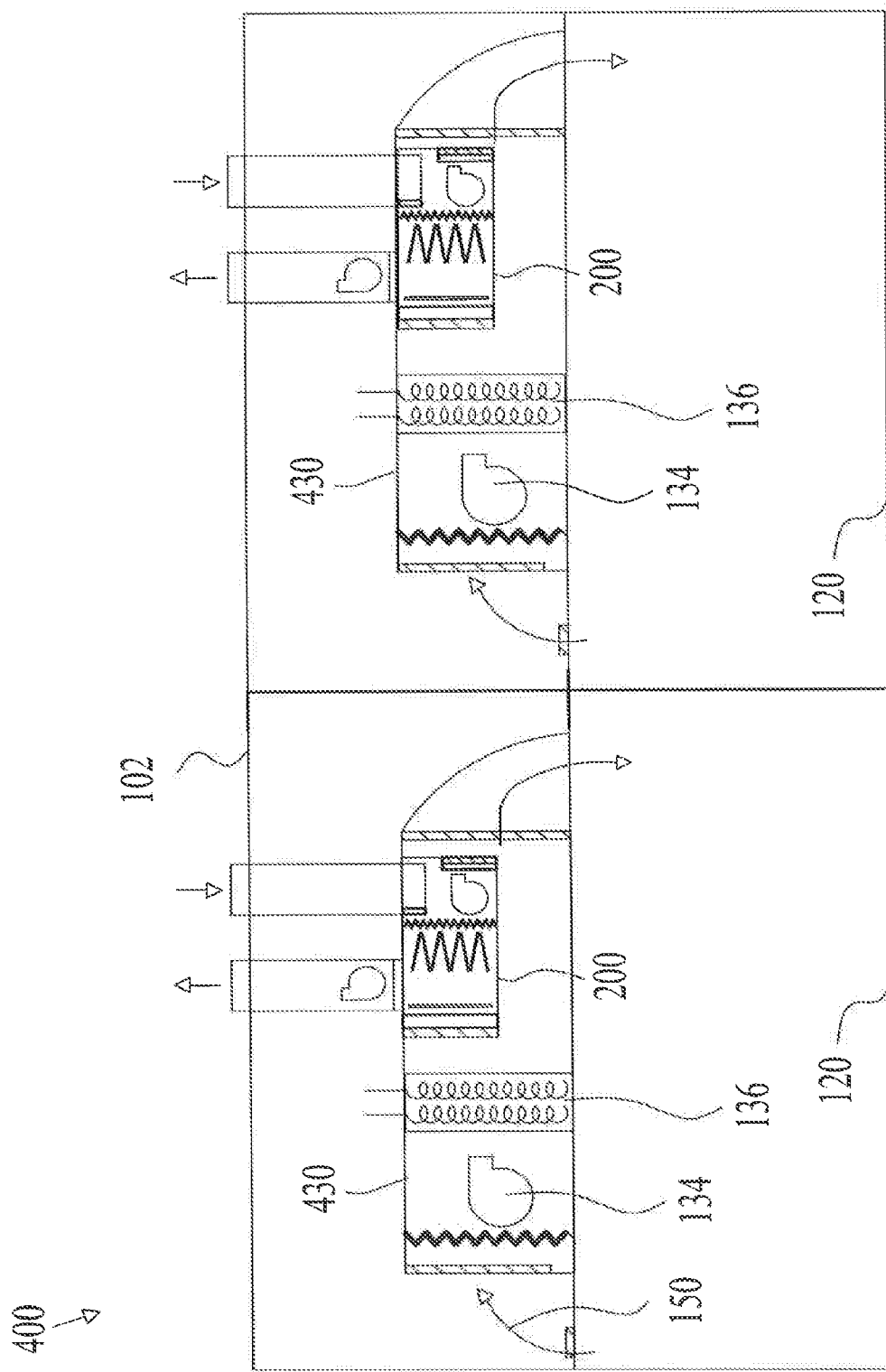

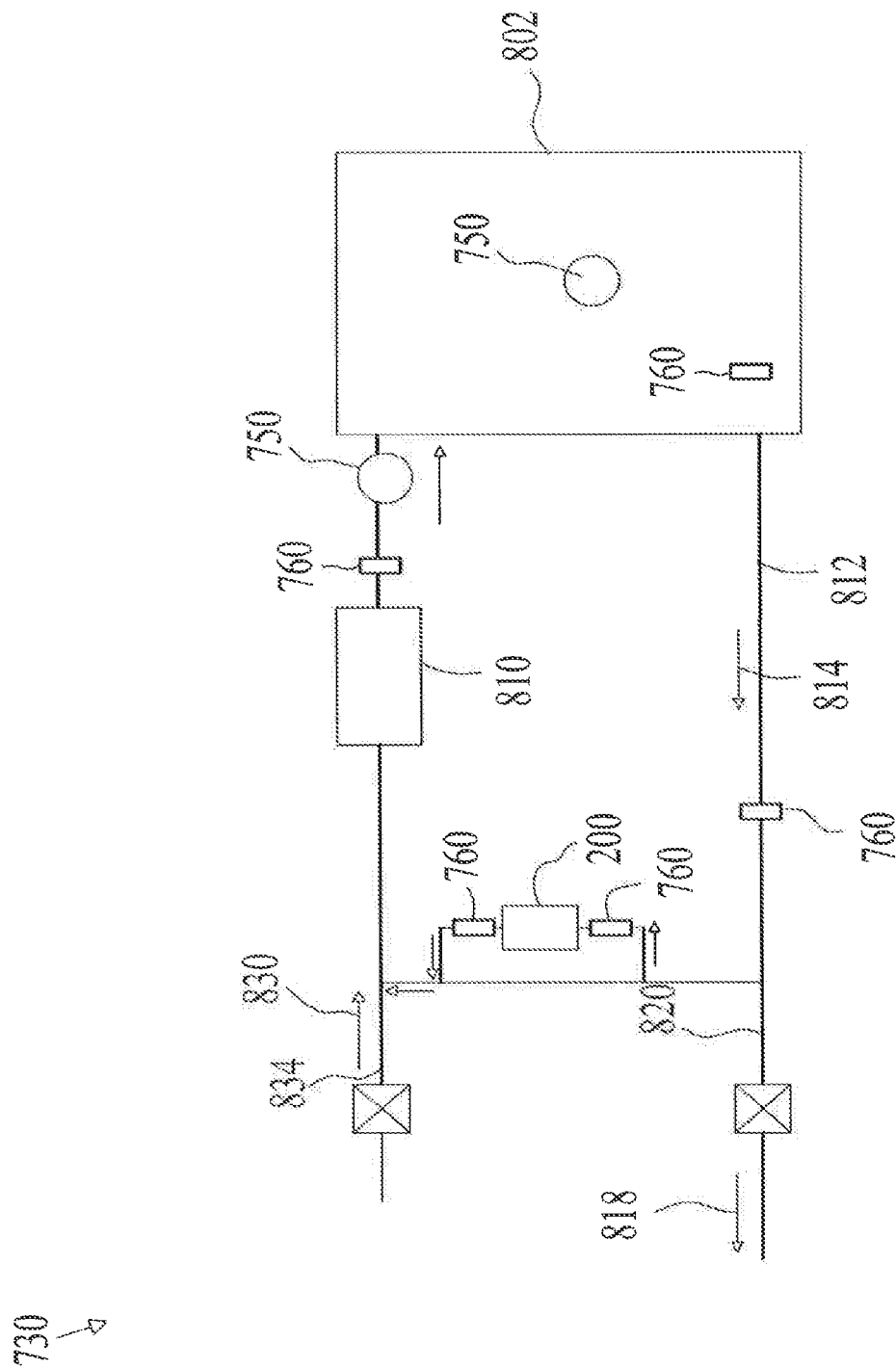

METHOD AND SYSTEM FOR CONDITIONING AIR IN AN ENCLOSED ENVIRONMENT WITH DISTRIBUTED AIR CIRCULATION SYSTEMS

CROSS REFERENCE TO RELATED APPLICATIONS

This application is a continuation of U.S. Non-provisional patent application Ser. No. 14/359,280, filed May 19, 2014 and entitled "Method And System For Conditioning Air In An Enclosed Environment With Distributed Air Circulation Systems," which is a national stage application of International Patent Application No. PCT/US2012/065600, filed Nov. 16, 2012, and entitled "Method And System For Conditioning Air In An Enclosed Environment With Distributed Air Circulation Systems," which in turn claims priority to: U.S. Provisional Patent Application No. 61/560,824, filed Nov. 17, 2011 and entitled "Method and System for Treating Air in an Enclosed Environment"; U.S. Provisional Patent Application No. 61/560,827, filed Nov. 17, 2011 and entitled "Method and System for Improved Air-Conditioning"; and U.S. Provisional Patent Application No. 61/704,850, filed Sep. 24, 2012 and entitled "Method and System for Treating Air in an Enclosed Environment with Distributed Air Circulation Systems". The disclosures of the above applications are incorporated herein by reference in their entireties.

TECHNICAL FIELD

The present application generally relates to systems for conditioning air in an enclosed environment and more particularly to systems for conditioning air in an enclosed environment comprising distributed air circulation systems.

BACKGROUND

Indoor air within and around enclosed environments, such as buildings, vehicles and structures, is affected by a plurality of contaminants. Among these contaminants, often with the highest concentration, is carbon dioxide ($CO_2$). There are other contaminants which may appear in relatively lower concentrations yet are no less important to monitor and/or reduce. A class of such contaminants is a group of species of organic vapors, broadly referred to as Volatile Organic Compounds (VOC). Contaminate gases (e.g., $CO_2$) and VOCs, and corresponding vapors thereof, may collectively be referred to as a "gas(es)". The sources of these contaminants include, inter alia, the human occupants themselves—from respiration and perspiration to clothing and cosmetics—as well as building materials, equipment, food and consumer products, cleaning materials, office supplies or any other materials which emit VOCs. Other classes of contaminants are inorganic compounds and microorganisms such as bacteria, viruses, mold, fungi and airborne particles. Additional gaseous contaminants may be sulfur oxides, nitrous oxides, radon, or carbon monoxide.

Heating, Ventilation and Air-Conditioning ("HVAC") is used in virtually every modern building. One of the goals of HVAC systems is to provide a comfortable and healthy environment for the enclosed environment occupants, in terms of temperature, humidity, composition and quality of air.

There are various HVAC system configurations known in the art.

A central HVAC system generally includes one or more central air handling units, which is operative to adjust the temperature or humidity of air received therein. The air exiting the central air handling unit is supplied to the enclosed environment via an air circulation system. In the central HVAC system the air circulation system is formed with ducts directing the supply air from the central air handling unit to various locations in the enclosed environment. In enclosed environments, such as buildings, comprising a plurality of indoor spaces, such as rooms, a network of ducts direct the supply air into each room. The air exiting the enclosed environment is returned to the central air handling unit.

As noted above, in order to maintain good air quality, not all the air is returned. Some of the air is exhausted out of the enclosed environment and is replaced by an intake of fresh air from the outside. This is sometimes referred to as "fresh air", "makeup air" or ventilation. Such replacement of the air dilutes the contaminants within the indoor air and helps maintain good air quality in the enclosed environment.

However, there are a number of drawbacks to fresh air ventilation, including the energy required to condition the outdoor air, as well as the potential introduction of pollutants and contaminants from the outside into the enclosed environment. One possible solution to these drawbacks is to selectively remove the contaminants from indoor air, and certain schemes have been proposed for this purpose in conjunction with central HVAC systems. For example, a system for removing the contaminants from indoor air in a central HVAC system is disclosed in applicant's U.S. Pat. No. 8,157,892, which is incorporated herein by reference in its entirety.

Selective contaminant removal from the central HVAC system is performed by directing the return air flowing within the ducts to a contaminant remover system and thereafter introducing the now treated return air back into the ducts. Generally the return air is directed to the contaminant remover system from the ducts directing the return air from the enclosed environment to the central air handling unit.

An alternative HVAC system is a distributed air circulation system. This distributed system generally conveys chilled (or heated) fluid to the plurality of indoor spaces, such as rooms, within the enclosed environment, where local air circulation units, such as fan-coil units circulate the indoor air. The fan-coil unit generally comprises a coil chilled (or heated) by the fluid. The coil is provided for adjusting the temperature or humidity of the circulated air and a fan or blower is provided for circulating the indoor air.

The chilled or heated fluid can originate from a centralized chilling or heating system shared by a plurality of fan-coil units, or from a single dedicated heat pump unit. As known in the art, the fluid can be supplied by a Variable Refrigerant Flow (VRF) system, a Fixed Refrigerant Flow system, or by a direct expansion (DX) system. In other distributed air circulation systems the fluid may be water.

The fan coil unit is placed within a room or space, typically within a recess in the ceiling or walls of the room. The fan coil unit may be placed in a plenum adjacent to the room. The circulating air flows from the air circulation unit into the room substantially without reliance on ducts (i.e. a ductless supply) and back from the room or space towards the air.

In order to maintain good air quality, some of the air is released out of the enclosed environment and is replaced by an intake of fresh outdoor air. Such replacement of the air dilutes the contaminants within the indoor air and helps maintain good air quality in the enclosed environment. The outdoor air generally enters the enclosed environment via a duct.

In some distributed air circulation systems, a central fresh air pre-conditioning unit initially cools (or heats) the outdoor air prior to entering ducts leading to the various rooms or fan-coil units inside the building. In other distributed air circulation systems the outdoor air directly enters the room, plenum or the air circulation unit wherein the outdoor air temperature is adjusted.

The energy required to condition the outdoor air, as well as the potential introduction of pollutants and contaminants from the outdoor into the enclosed environment are significant deficiencies of the outside air ventilation in these systems.

Embodiments of the present disclosure are directed to remedy these deficiencies.

SUMMARY

There is thus provided according to some embodiments of the present disclosure a system for conditioning air in a building including a fan-coil unit arranged adjacent to or within an indoor space within the building and additionally configured to at least one of heat and cool the air of the indoor space, and a scrubber arranged adjacent to or within the indoor space, the scrubber configured during a scrub cycle for scrubbing of indoor air from the indoor space. The scrubber includes one or more adsorbent materials arranged therein to adsorb at least one predetermined gas from the indoor air during the scrub cycle, a source of outdoor air, and an exhaust, wherein the scrubber is configured during a purge cycle to direct a purging air flow received from the source of outdoor air over and/or through the adsorbent materials to purge at least a portion of the at least one predetermined gas adsorbed by the adsorbent materials during the scrub cycle from the adsorbent materials and thereafter exhausting the flow via the exhaust.

According to some embodiments of the present disclosure, the fan-coil unit may be supplied a refrigerant or heating fluid from a Variable Refrigerant Flow (VRF) system. The fan-coil unit may be supplied chilled or heated water from a central chiller or boiler. Flow of indoor air from the indoor space to the scrubber or from the scrubber to the indoor space may be ductless. The predetermined gas may include carbon dioxide, volatile organic compounds, sulfur oxides, radon, nitrous oxides or carbon monoxide. The at least one of the adsorbent materials may include granular adsorbent particles, solid supported amines, activated carbon, clay, carbon fibers, carbon cloth, silica, alumina, zeolite, synthetic zeolite, hydrophobic zeolite, natural zeolite, molecular sieves, titanium oxide, polymers, porous polymers, polymer fibers or metal organic frameworks. At least one of the adsorbent materials may be contained in one or more removable cartridges. At least one gas detection sensor for detecting a level of the at least one predetermined gas may be provided.

According to some embodiments of the present disclosure, the scrubber may further include at least one of a damper and a fan configured to switch the scrubber from the scrub cycle to the purge cycle. The system may further include a controller to perform the switching, wherein the controller is programmed to switch between the scrub cycle and the purge cycle by at least one of a preset schedule, a predetermined level of the predetermined gas, the indoor space occupancy level, a manual trigger, a signaled command or an externally signaled command. The system may further include an air plenum over a ceiling of the indoor space or adjacent to the indoor space, wherein the air plenum houses the fan-coil unit. The system may further include an air plenum over a ceiling of the indoor space or adjacent to the indoor space, wherein the air plenum houses the scrubber.

According to some embodiments of the present disclosure, the fan-coil unit may include housing, and wherein at least a portion of the scrubber may be housed within the housing. A fan of the fan-coil unit may be configured to direct indoor air flow into the scrubber. The system may further include a heater, wherein the received outdoor air is heated by the heater. The heater may be a heat pump, an electric heating coil, a coil or radiator with heated fluid supplied from a central heating system, a solar heater or a furnace. The heat pump may remove heat from the indoor air. The heated outdoor air may be heated prior to being supplied to the scrubber.

According to some embodiments of the present disclosure, the system may include at least one additional air treatment component such as an air ionizer, an ozone source, a source of radiation, a membrane, foam, paper, fiberglass, a heater, a particle filter, an ultraviolet anti-microbial device, an ion or plasma generator, an oxide, a catalyst or a chemical catalyst. The additional air treatment component may be placed within the scrubber. The additional air treatment component may be placed within the indoor space. The indoor air flows out of the fan-coil unit via a duct and the additional air treatment component may be placed within the duct.

According to some embodiments of the present disclosure, a plurality of indoor spaces may be provided and a plurality of fan-coil units may be provided. The plurality of fan-coil units may be arranged adjacent to or within the plurality of indoor spaces and the scrubber may be configured during a scrub cycle for scrubbing of indoor air from the plurality of indoor spaces.

There is thus provided according to some embodiments of the present disclosure an air treatment system for conditioning air in a building, including a scrubber configured during a scrub cycle for scrubbing of air from an indoor space of the building and positioned within or adjacent the indoor space, the scrubber including one or more adsorbent materials arranged therein to adsorb at least one predetermined gas from the air of the indoor space during the scrub cycle, a source of outdoor air, and an exhaust, wherein the scrubber is configured during a purge cycle to direct a purging air flow, received via the source of outdoor air, over and/or through the adsorbent materials to purge at least a portion of the at least one predetermined gas adsorbed by the adsorbent materials during the scrub cycle from the adsorbent materials and thereafter exhausting the flow, via the exhaust.

According to some embodiments of the present disclosure, the scrubber may be configured to supply scrubbed air exiting the scrubber to the indoor space. The scrubber may be configured to supply scrubbed air to a fan-coil unit arranged adjacent to or within the indoor space.

There is thus provided according to some embodiments of the present disclosure a method for conditioning air in a building, including circulating indoor air of an indoor space via a fan-coil unit, optionally heating or cooling the circulated indoor air, scrubbing the indoor air during a scrub cycle using a scrubber placed within or adjacent to the indoor space, the scrubber including one or more adsorbent materials arranged therein to adsorb at least one predetermined gas from the air of the indoor space during the scrub cycle, a source of outdoor air, and an outdoor exhaust, flowing a purging air flow received via the source of outdoor air over and/or through the one or more adsorbent materials so as to purge the adsorbent materials of at least a portion of the at least one gas adsorbed by the one or more adsorbent materials, and thereafter exhausting the purging air flow via the exhaust.

There is thus provided according to some embodiments of the present disclosure a system for conditioning air in a building including a plurality of indoor spaces within the building, a plurality of fan-coil units arranged adjacent to or within the plurality of indoor spaces and additionally configured to at least one of heat and cool the air of the plurality of indoor spaces, and a scrubber arranged adjacent to or within the building, the scrubber configured during a scrub cycle for scrubbing of indoor air from the plurality of indoor spaces, the scrubber including one or more adsorbent materials arranged therein to adsorb at least one predetermined gas from the indoor air during the scrub cycle, a source of outdoor air, and an exhaust, wherein the scrubber is configured during a purge cycle to direct a purging air flow received from the source of outdoor air over and/or through the adsorbent materials to purge at least a portion of the at least one predetermined gas adsorbed by the adsorbent materials during the scrub cycle from the adsorbent materials and thereafter exhausting the flow via the exhaust.

According to some embodiments of the present disclosure, the fan-coil unit may be supplied refrigerant or heating fluid from a variable refrigerant flow (VRF) system. More than one of the plurality of fan-coil units may be supplied refrigerant or heating fluid from a common variable refrigerant flow (VRF) system. The fan-coil unit may be supplied chilled or heated water from a central chiller or boiler. Scrubbed air exiting the scrubber may be directed to the plurality of indoor spaces via conduits. Indoor air may be directed to the scrubber from the plurality of indoor spaces via conduits. The conduits may be installed and configured for directing the indoor air from the plurality of indoor spaces to the scrubber. The conduits may be pre-existing in the building and may be configured for ventilation, elevators exhaust or smoke exhaust in the building. A pre-conditioning unit may be configured to at least heat or cool outside air or scrubbed air exiting the scrubber and direct the pre-conditioned air to the plurality of indoor spaces. The pre-conditioned air may be directed to the plurality of indoor spaces via conduits.

BRIEF DESCRIPTION OF THE DRAWINGS

The principles and operations of the systems, apparatuses and methods according to some embodiments of the present disclosure may be better understood with reference to the drawings, and the following description. These drawings are given for illustrative purposes only and are not meant to be limiting.

FIGS. 9A-9E are each a simplified schematic illustration of still another system for conditioning air in an enclosed environment according to some embodiments of the present disclosure;

FIGS. 11A-11D are each a simplified schematic illustration of another system for conditioning air in an enclosed environment according to some embodiments of the present disclosure.

DETAILED DESCRIPTION

Figure 1:
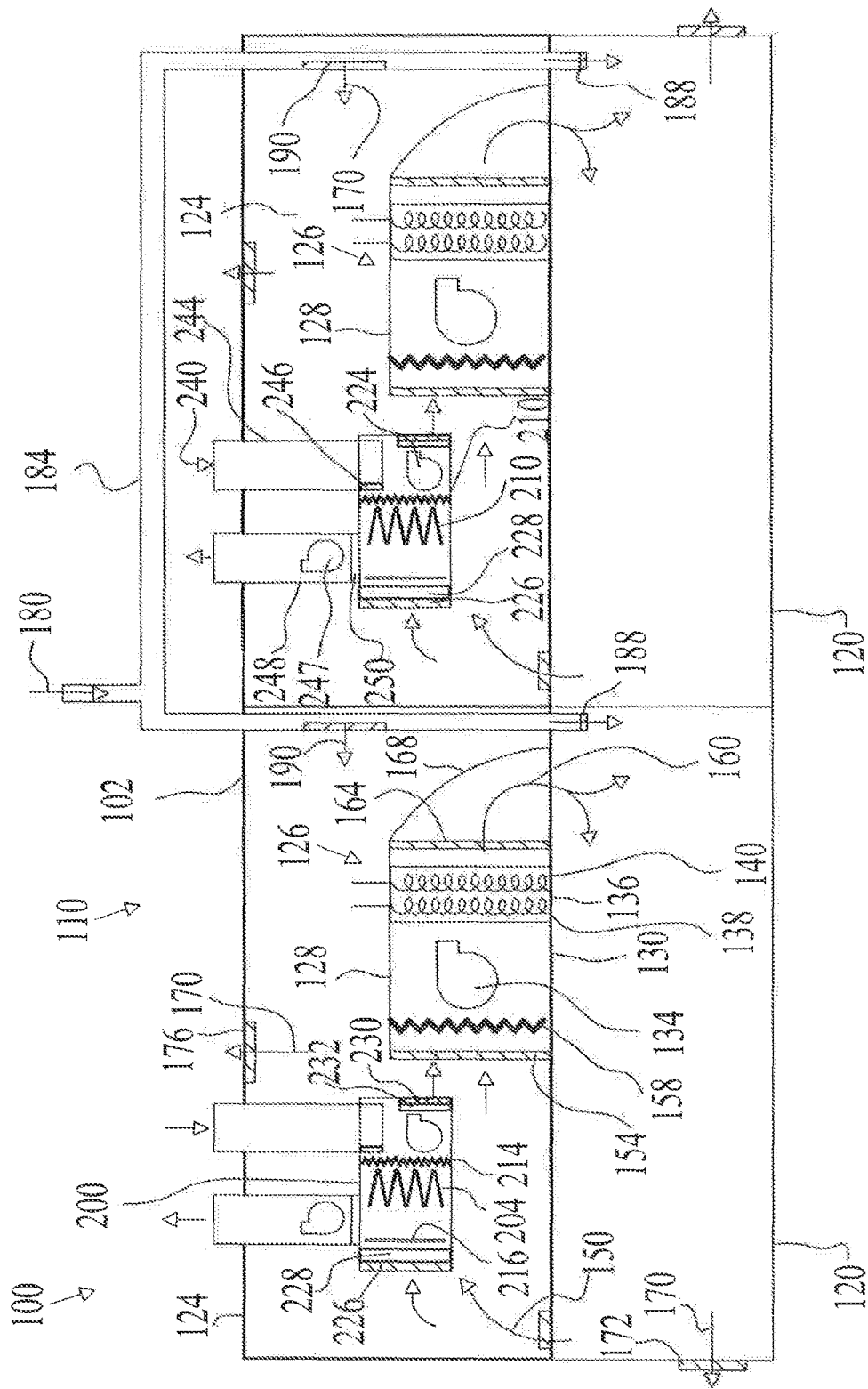
FIG. 1 is a simplified schematic illustration of a system for conditioning air in an enclosed environment according to some embodiments of the present disclosure.
Figure 2:
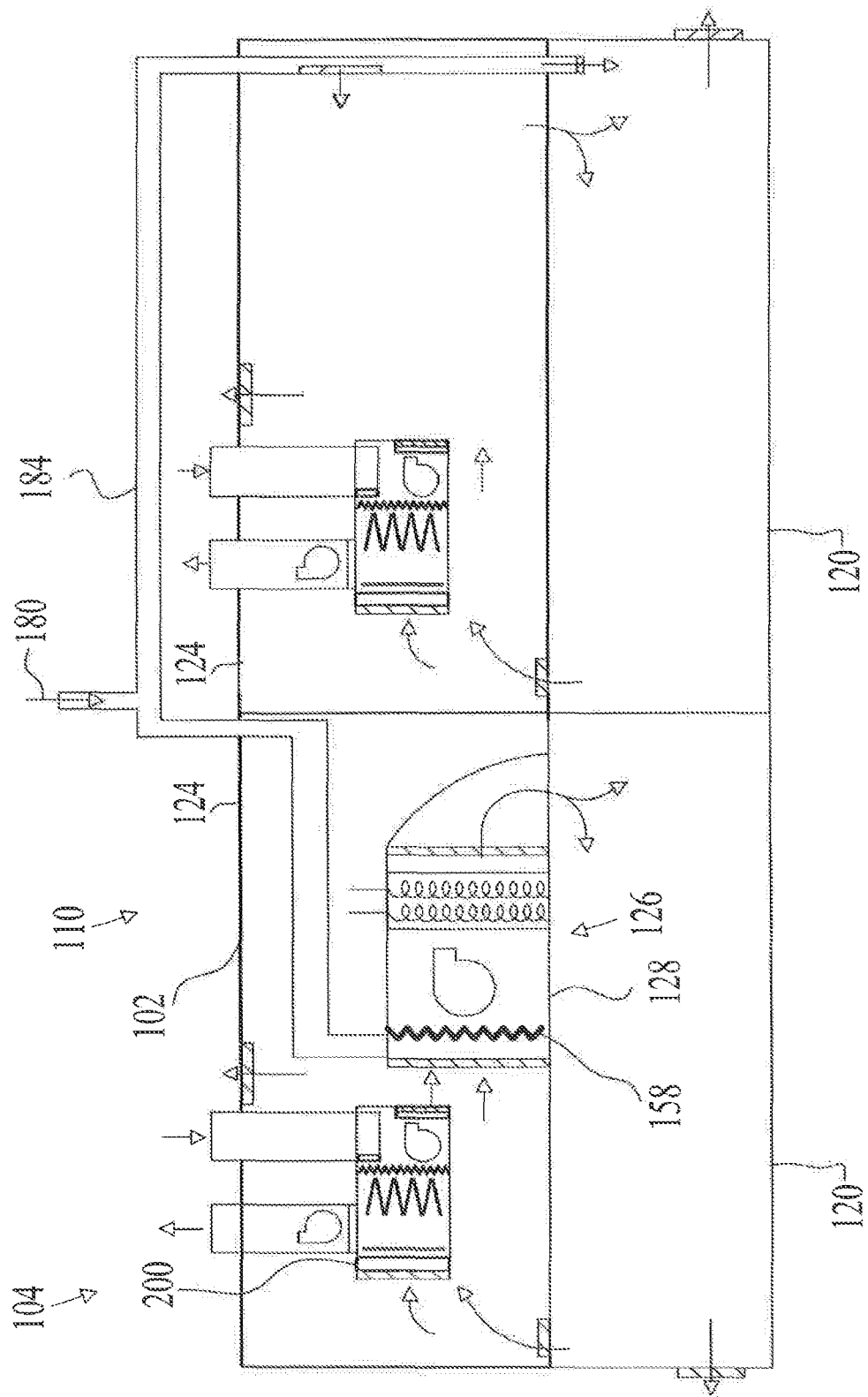
FIG. 2 is a simplified schematic illustration of another system for conditioning air in an enclosed environment according to some embodiments of the present disclosure.
Figure 3:
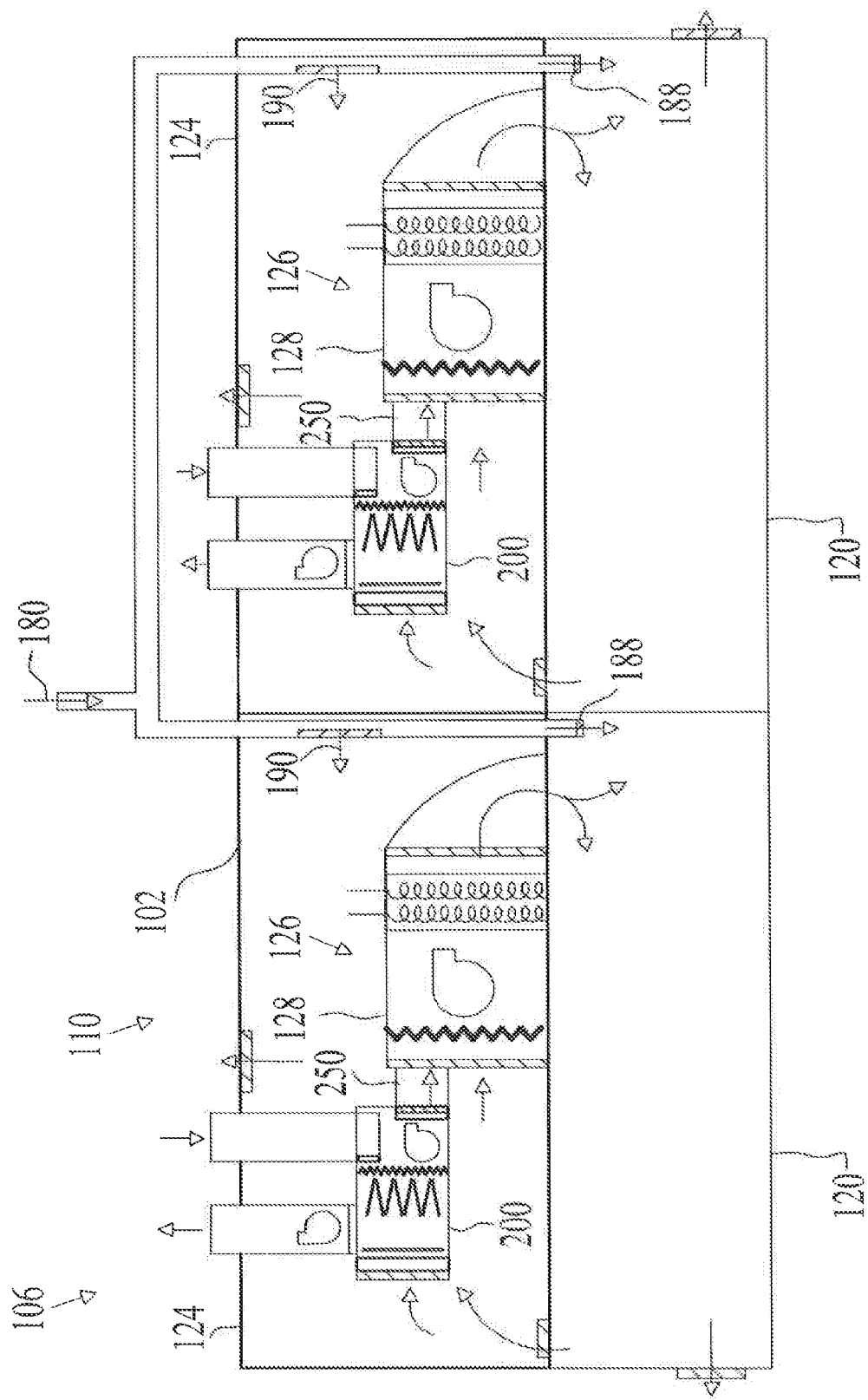
FIG. 3 is a simplified schematic illustration of yet another system for conditioning air in an enclosed environment according to some embodiments of the present disclosure.

FIG. 1 is a simplified schematic illustration of a system 100 for conditioning air in an enclosed environment 102 (e.g., the interior of a building) according to some embodiments of the present disclosure. FIG. 2 is another simplified schematic illustration of a system 104 for conditioning air in the enclosed environment 102 according to some embodiments of the present disclosure, and FIG. 3 is yet another simplified schematic illustration of a system 106 for conditioning air in the enclosed environment 102 according to some embodiments of the present disclosure. As seen in FIGS. 1-3, the respective systems 100, 104 and 106 for conditioning air in the enclosed environment 102 each comprise a distributed air circulation system 110.

The enclosed environment 102 may comprise an office building, a commercial building, a bank, a residential building, a house, a school, a factory, a hospital, a store, a mall, an indoor entertainment venue, a storage facility, a laboratory, a vehicle, an aircraft, a ship, a bus, a theatre, a partially and/or fully enclosed arena, an education facility, a library and/or other partially and/or fully enclosed structure and/or facility which can be at times occupied by equipment, materials, live occupants (e.g., humans, animals, synthetic organisms, etc.) and/or any combination thereof.

According to some embodiments, the enclosed environment 102 may comprise a plurality of indoor spaces 120, such as rooms, cubicles, zones in a building, compartments, railroad cars, caravans or trailers, for example. Adjacent to the indoor space 120 may be an air plenum 124, typically located above the ceiling of the indoor space 120. As seen in FIG. 1, each indoor space 120 is associated with a separate air plenum 124, though a common air plenum 124 may be associated with a plurality of indoor spaces 120.

According to another embodiment, the enclosed environment 102 may comprise a single indoor space 120. An exemplary enclosed environment 102 comprising a single indoor space 120 will be further described in reference to FIG. 7.

The distributed air circulation system 110 conveys chilled or heated fluid to local air circulation units 126. Typically, nearly each indoor space 120 is associated with a local air circulation unit 126, which circulates and cools or heats the indoor air of the indoor space 120. As seen in FIGS. 1 and 3, each indoor space 120 is associated with an air circulation unit 126. In FIG. 2 only the left side indoor space 120 is associated with an air circulation unit 126.

In the embodiments shown in FIGS. 1-11C the air circulation unit 126 comprises a fan-coil unit 128. It is appreciated that the air circulation unit 126 may comprise any other suitable device for circulating and cooling or heating air in indoor spaces 120, such as a blower-coil unit, for example. In some embodiments the air circulation unit 126 may be a component in a split unit system.

The chilled or heated fluid may originate from a centralized chilling or heating system shared by a plurality of air circulation units, or from a single dedicated heat pump or boiler (not shown). In accordance with some embodiments, the fluid may be supplied by a Variable Refrigerant Flow (VRF) system. In accordance with another embodiment the fluid may be supplied by a Fixed Refrigerant Flow system or by a direct expansion (DX) system. In other distributed air circulation systems the fluid may be water.

The fan-coil unit 128 may comprise a housing 130 including a fan 134 and coils 136. The coils 136 are typically cooled or heated by the fluid. The coils 136 may comprise a cooling coil 138 and/or a heating coil 140 and/or any other suitable cooling or heating means, such as radiators, electrical heaters, chillers, heat exchangers, nozzles or jets, for example.

At least a portion of the indoor air may exit the indoor space 120 as return air 150. In accordance with some embodiments, the return air may enter the air plenum 124. Typically the return air 150 enters the air plenum 124 without flowing through a duct, though in some embodiments a duct (not shown) may be provided.

In accordance with other embodiments the indoor space 120 may be associated with an adjacent area above its ceiling instead of the air plenum 124. The return air 150 may flow within a duct (not shown) located in the area above the ceiling to the fan-coil unit 128.

The fan 134 draws the return air 150 to enter fan-coil unit 128, via an entry port 154, and flow in the vicinity of coils 136 for heating or cooling thereof. In FIGS. 1-3 the coils 136 are placed downstream the fan 134. Alternatively, the coils 136 may be placed intermediate the fan 134 and the entry port 154 or at any other suitable location. Return air 150 may flow through a particle filter 158 for removing dust and airborne particles therefrom.

Conditioned air 160, i.e. return air cooled or heated by the coils 136, exits via an exit port 164. The conditioned air 160 enters the indoor space 120 for circulation thereof. The conditioned air 160 may flow from the fan-coil unit 128 into the indoor space via a duct 168 or may ductlessly flow into the indoor space 120.

A portion of the indoor air may be exhausted from the enclosed environment 102 as exhaust air 170 into the ambient or any location outside the enclosed environment 102. Any suitable means, such as a blower or a fan (not shown) may be used to exhaust the exhaust air 170. The exhaust air 170 may exit the indoor space 120, via an exhaust port 172, and/or may exit the air plenum 124, via an exhaust port 176 or via an exhaust port (not shown) of the fan-coil unit 128.

In standard distributed air circulation systems fresh, outdoor air or namely "makeup air" 180 may be introduced into the enclosed environment 102 for supplying nominally fresh, good quality air combining with the return air 150. The outdoor air 180 may be introduced into the enclosed environment in any suitable manner, such as by a network of ducts 184. In the embodiment shown in FIGS. 1 and 3 the outdoor air 180 may be introduced directly into each of the indoor spaces 120, via an entry port 188, or the outdoor air 180 may be introduced into the air plenum 124, via an entry port 190. In another embodiment, the outdoor air 180 may be introduced directly into each fan-coil unit 128, as shown in FIG. 2. As seen in FIG. 2, the duct 184 is directed to introduce the outdoor air 180 into the fan-coil unit 128 prior to the particle filter 158, though the outdoor air 180 may be introduced into the fan-coil unit 128 at any suitable location therein.

A scrubber 200 is provided to reduce the concentration of contaminants present in the return air 150 flowing therein. A contaminant may be a predetermined gas or vapor, such as $CO_2$, for example. The scrubber 200 may comprise a $CO_2$ scrubber 204. Examples of $CO_2$ scrubbers are disclosed in applicant's U.S. Pat. No. 8,157,892, which is incorporated herein by reference in its entirety. The $CO_2$ scrubber 204 may comprise any suitable material for capturing $CO_2$, such as a $CO_2$ adsorbent material. An exemplary $CO_2$ adsorbent material may be a solid support material supporting an amine-based compound, such as disclosed in applicant's PCT application PCT/US12/38343, which is incorporated herein by reference in its entirety. Other adsorbent materials include, but are not limited to, granular adsorbent particles, clay-based adsorbents, activated carbon, zeolites, natural zeolite, activated charcoal, molecular sieves, silica, silica gel, porous silica, alumina, porous alumina, titanium oxide, carbon fibers, porous polymers, polymer fibers and metal organic frameworks.

The $CO_2$ scrubber 204 may include a plurality of $CO_2$ scrubbing cartridges 210. The $CO_2$ scrubbing cartridges 210 may comprise the adsorbent material formed as a solid or flexible sheet or as granules supported by porous surfaces. The scrubbing cartridges 210 may be arranged in any suitable arrangement. For example, the $CO_2$ scrubbing cartridges 210 may be parallelly arranged therebetween. Alternatively, as seen in FIG. 1, the $CO_2$ scrubbing cartridges 210 may be staggeringly arranged therebetween. This staggered arrangement allows substantially parallel air flow paths of the return air 150 therethrough. Exemplary $CO_2$ scrubbing cartridges and modules are disclosed in applicant's US Patent Publication No. 20110198055, which is incorporated herein by reference in its entirety.

An additional contaminant may be VOCs. The scrubber 200 may comprise a VOC scrubber 214 for removing VOCs from the return air 150 flowing therethrough. The VOC scrubber 214 may comprise any suitable adsorbent material for adsorbing the VOCs. For example VOC adsorbent materials may comprise a hydrophobic zeolite, natural zeolite, synthetic zeolite, carbon cloth, activated carbon, a molecular sieve, polymers, a thin permeable sheet structure, carbon fibers, or granular adsorbent particles attached to a sheet of some other permeable material, such as paper, cloth or fine mesh, for example.

The VOC scrubber 214 may be arranged in any suitable arrangement, such as a bed of granular material, a flat sheet, or a pleated sheet, as shown in FIG. 1.

A filter 216 may be provided for removing additional contaminants, such as dirt, small airborne particles and may comprise any suitable filter or adsorbent material.

Operation of the scrubber 200 may comprise a scrub cycle and a purge cycle. During the scrub cycle, the contaminants are captured and adsorbed by the adsorbent material or any other means. A portion of the return air 150 may be urged by a scrubber fan 224 to flow into the scrubber 200. The return air 150 may flow into the scrubber 200 via an entry port 226 including an entry damper 228, when positioned in an open state.

The volume of the portion of the return air 150 flowing into the scrubber 200 may be controlled by the scrubber fan 224 and/or damper 228, or by any other suitable means. In some embodiments, a volume of approximately 1%-50% of the fan-coil airflow (namely air flowing through the fan-coil unit 128) may enter the scrubber 200. In some embodiments, a volume of approximately 1%-25% of the fan-coil airflow may enter the scrubber 200. In some embodiments, a volume of approximately 1%-10% of the fan-coil airflow may enter the scrubber 200. The remaining return air 150, which bypassed the scrubber 200, may flow directly through the fan-coil unit 128 or to the indoor space 120.

The scrubber fan 224 may be placed in any suitable location within the scrubber 200, such as upstream in a "push" mode, i.e. intermediate the entry port 226 and the $CO_2$ scrubber 204. Alternatively, as seen in FIG. 1, the scrubber fan 224 may be placed downstream in a "pull" mode i.e. after the $CO_2$ scrubber 204.

The return air 150 may flow through the filter 216, $CO_2$ scrubber 204 and/or the VOC scrubber 214. The now scrubbed air flows out of the scrubber 200 via an exit port 230 including an exit damper 232, when positioned in an open state. The scrubbed air flows into the fan-coil unit 128 and may be conditioned by being cooled or heated therein. The conditioned air 160 may flow from the fan-coil unit 128 into the indoor space 120.

Scrubbing the return air within the scrubber 200, according to some embodiments, allows reducing or eliminating the volume of fresh, outdoor air 180, which is required to provide for maintaining good air quality therein. Accordingly, the energy required to condition the outdoor air 180 is reduced or eliminated. Additionally, introduction of potential pollutants and contaminants from the outdoor air 180 into the enclosed environment 102 is reduced or eliminated. In some embodiments the volume of fresh, outdoor air 180 may be reduced approximately to a minimally required volume of the exhausted air 170, so as to maintain pressure equilibrium within the enclosed environment 102. Moreover, superior indoor air quality is provided.

The volume of fresh, outdoor air 180 may be reduced in any suitable manner such as by reducing the volume of outdoor air 180 prior to flow in ducts 184 or by partially or fully closing dampers (not shown) within the enclosed environment 102 for controlling the volume of outdoor air 180 introduced therein.

Following the capture and scrubbing of the contaminants in the scrub cycle, the adsorbent material may be regenerated during the purge cycle by urging the release of the contaminants from the adsorbent material.

The regeneration may be performed in any suitable manner. For example, in some embodiments, regeneration may be performed by streaming a purge gas 240 over and/or through the adsorbent material for release of at least a portion of the contaminants therefrom.

For example, during the purge cycle the purge gas 240 flows into the scrubber 200 via an entry conduit 244 including an entry damper 246, when positioned in an open state, while the entry damper 228 and exit damper 232 may be closed. A fan 247 may be provided for urging flow of the purge gas 240 within the scrubber 200. The fan 247 may be placed in any suitable location, such as in an exhaust conduit 248. Alternatively, the fan 247 may be omitted.

Thus, in some embodiments, it is seen that switching the scrubber operation from the scrub cycle to the purge cycle may be performed by the dampers and/or fans or any other suitable means.

In accordance with some embodiments the purge gas 240 comprises outdoor air.

The outdoor air may be provided to the scrubber 200 from any source of outdoor air. For example, the source of outdoor air may be ambient air flowing directly from the ambient, i.e. out of the enclosed environment 102, into the scrubber 200, as shown in FIG. 1. Alternatively, the outdoor air may flow from the ambient into the scrubber 200 via ducts (not shown). Additionally, the source of outdoor air may be from other locations near the space 120, such as from a pier or elevator shaft.

As shown in FIGS. 1-3, in some embodiments, the purge gas 240 may flow during the purge cycle in the opposite direction of the return air flow during the scrub cycle, such as from entry conduit 244 to the exhaust conduit 248. Alternatively, the purge gas 240 may flow during the purge cycle in the same direction of the return air flow, such as from exhaust conduit 248 to entry conduit 244.

The exhaust conduit 248 may include an exit damper 250.

It is noted that the entry conduit 244 may be replaced by an aperture allowing the purge gas 240 to flow into the scrubber 200. The exhaust conduit 248 may be replaced by any exhaust allowing the purge gas 240 to flow out of the scrubber 200.

As seen in FIGS. 1-11C, in some embodiments, the purge gas 240 exiting the exhaust conduit 248 is discharged into the ambient, out of the enclosed environment 102. Alternatively, the purge gas 240 may flow out of the exhaust conduit 248 to existing exhaust ducts in the enclosed environment such as an air exhaust typically furnished in a bathroom of the enclosed environment 102 or openings such as windows. Additionally, purge gas 240 exiting the exhaust conduit 248 may flow to a volume in the enclosed environment 102, such as a stairwell, sewerage system or smoke control systems. Moreover, purge gas 240 may be directed to flow into a pressure vessel (not shown) for eventual release of the purge gas 240 therefrom.

Figure 10A:
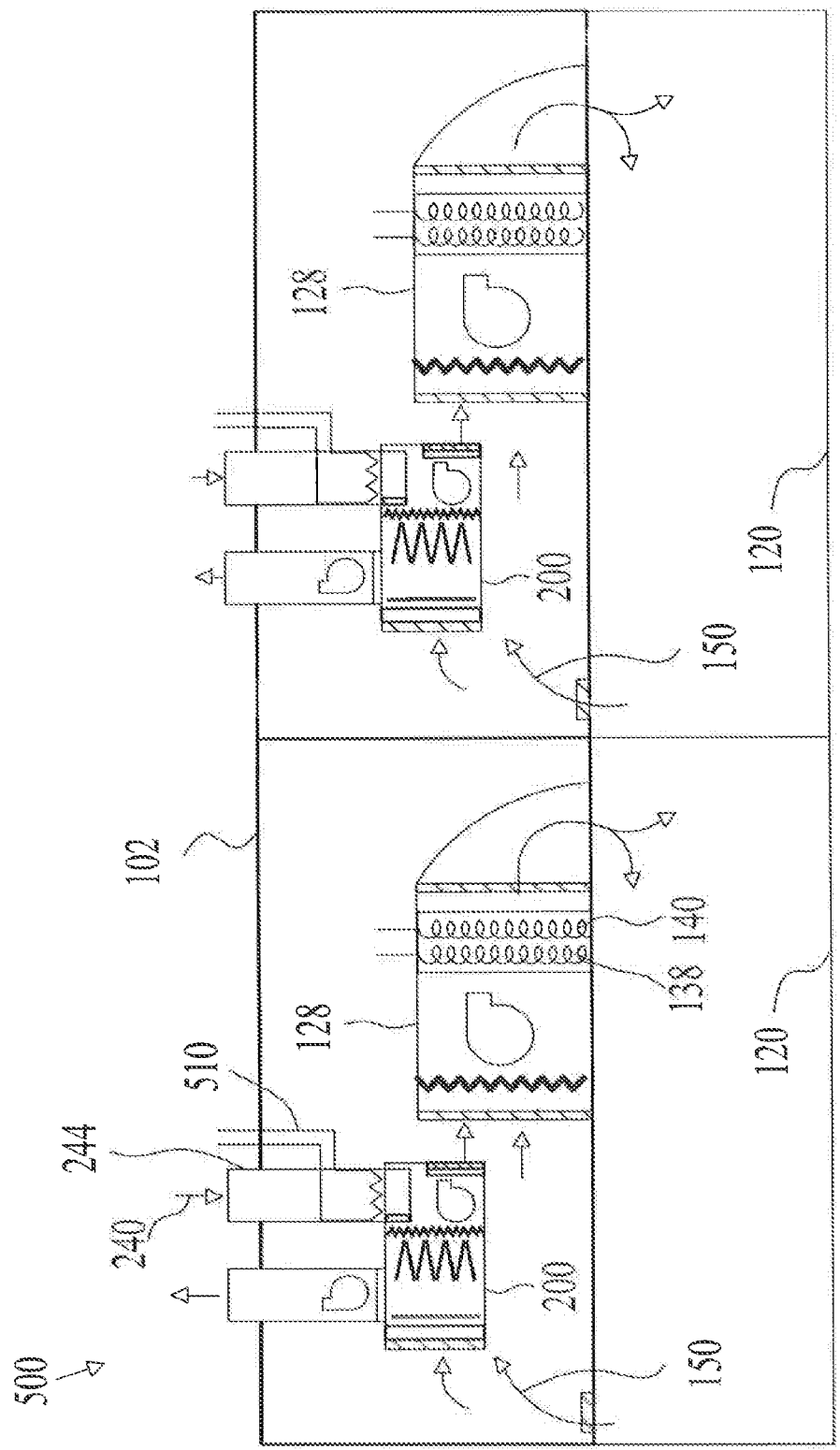
FIGS. 10A and 10B are each a simplified schematic illustration of another system for conditioning air in an enclosed environment according to some embodiments of the present disclosure.
Figure 10B:
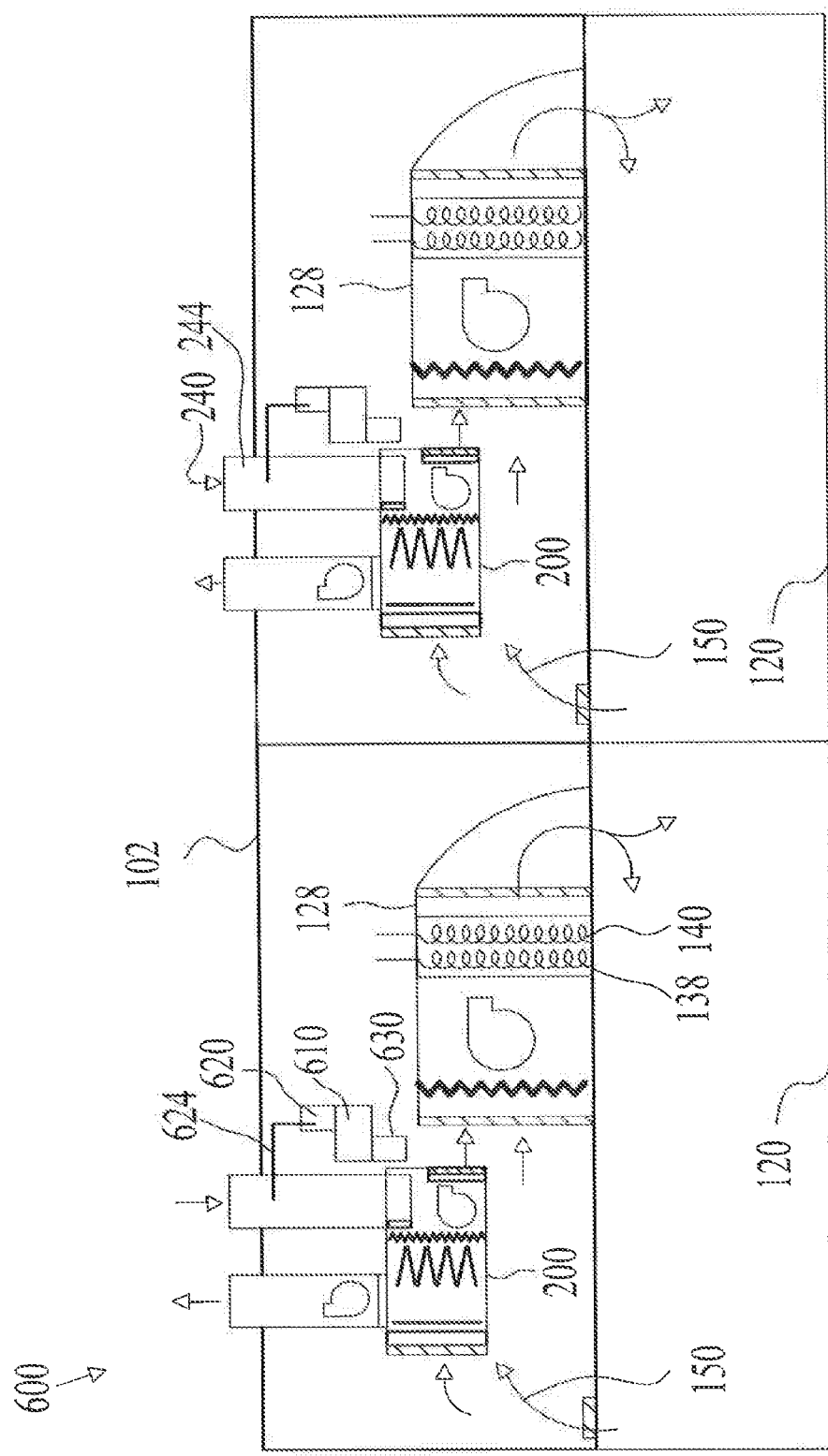

The purge gas 240 may be heated prior to regeneration of the scrubber 200 by any suitable method, as will be further described in reference to FIGS. 10A and 10B.

In accordance with some embodiments, the purge gas 240 may be heated within a range of approximately 20-120° C. In accordance with some embodiments, the purge gas 240 may be heated to a temperature of less than 80° C. In accordance with some embodiments, the purge gas 240 may be heated to a temperature of less than 50° C. In accordance with some embodiments, the purge gas 240 may enter the scrubber 200 at the ambient temperature.

Regeneration of the adsorbent material removes the contaminants from the adsorbent material. Therefore, the scrubber 200 can be repeatedly used for removing contaminants from the indoor space 120 without requiring replacement of the adsorbent material. Accordingly, the scrubber 200 described herein has a significantly long operating life.

In the distributed air circulation system 110, according to some embodiments, the flow of the return air 150 into and out of the scrubber 200 and into and out of the fan-coil unit 128 may be at least partially ductless. For example, as shown in FIGS. 1-3, the flow of the return air 150 into the scrubber 200 is ductless and a portion of the return air 150 is urged by the scrubber fan 224 to flow from the air plenum 124 into the scrubber 200. The flow of the return air 150 from the air plenum 124 into the fan-coil unit 128 is shown to be ductless and is urged by the fan 134 to flow therein. The flow of the conditioned air out of the fan-coil unit 128 may be ductless or, as shown in FIGS. 1-3, the duct 168 is provided.

In some embodiments, such as seen in FIGS. 1 and 2, the scrubbed air exiting the scrubber 200 may flow into the air plenum 124 and enter into the fan-coil unit 128 without a duct.

In other embodiments, as seen in FIG. 3, the scrubbed air exiting the scrubber 200 may flow into the fan-coil unit 128 via a duct 250.

Figure 4:
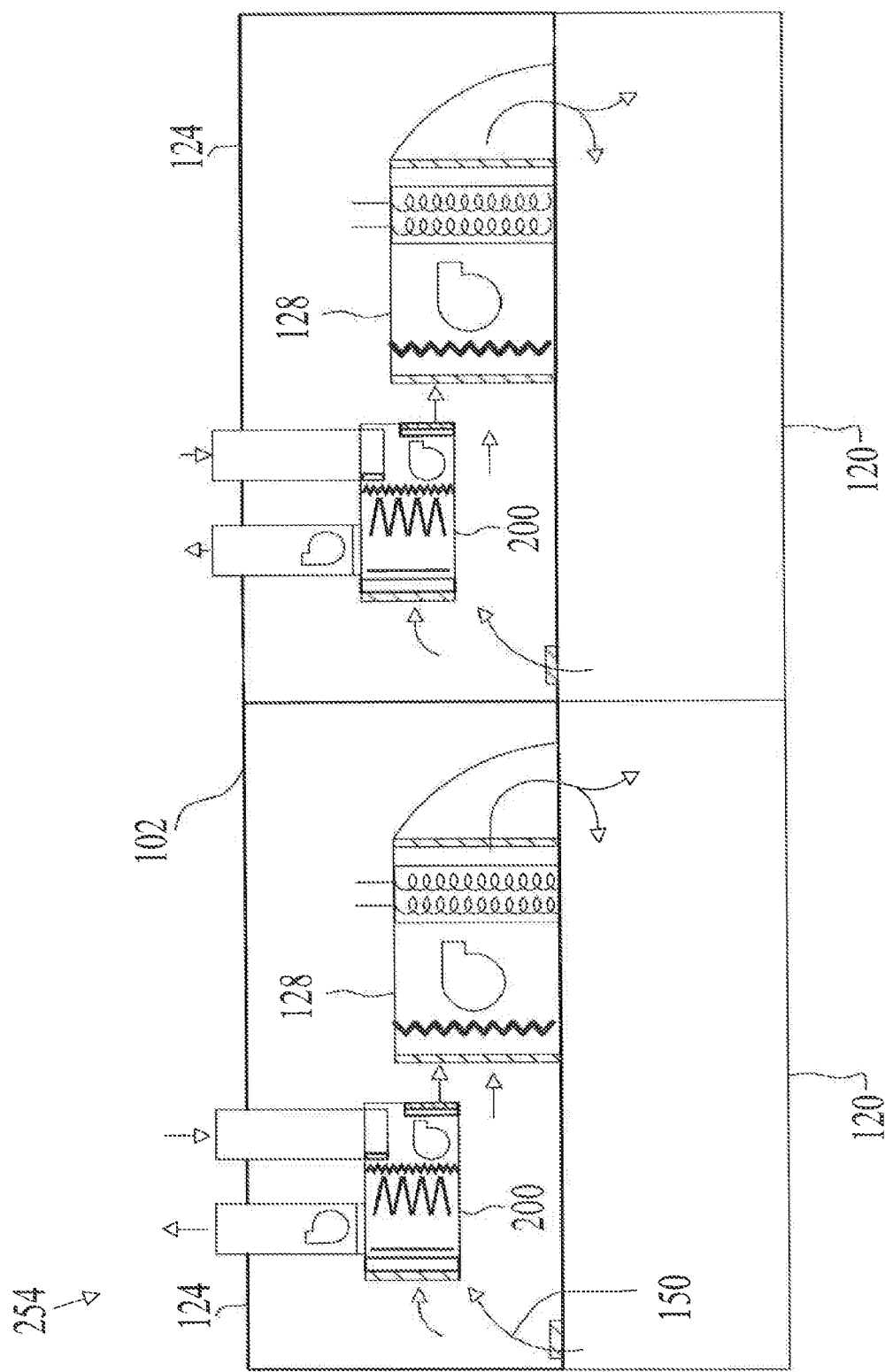
FIG. 4 is a simplified schematic illustration of still another system for conditioning air in an enclosed environment according to some embodiments of the present disclosure.

In FIG. 4, a system 254 for conditioning air in the enclosed environment 102 is substantially similar to the respective systems 100, 104 and 106 of FIGS. 1-3. As seen in FIG. 4, exhaust ports 172 or 176 are not included and similarly outdoor air 180 is not introduced into the indoor spaces 120 or the air plenum 124. A portion of the return air 150 is scrubbed in the scrubber 200, thereby providing good air quality to the indoor space 120. Therefore, introduction of the fresh, outdoor air 180 for maintaining good air quality is unnecessary and the energy required to condition the outdoor air 180 is also eliminated. Additionally, introduction of potential pollutants and contaminants from the outdoor air 180 into the enclosed environment 102 is eliminated.

A portion of the return air 150 may initially flow to the scrubber 200 and thereafter the scrubbed air may flow into the fan-coil unit 128, as shown in FIGS. 1-4. Alternatively, the return air 150 may initially flow through the fan-coil unit 128, as shown in FIG. 5.

Figure 5:
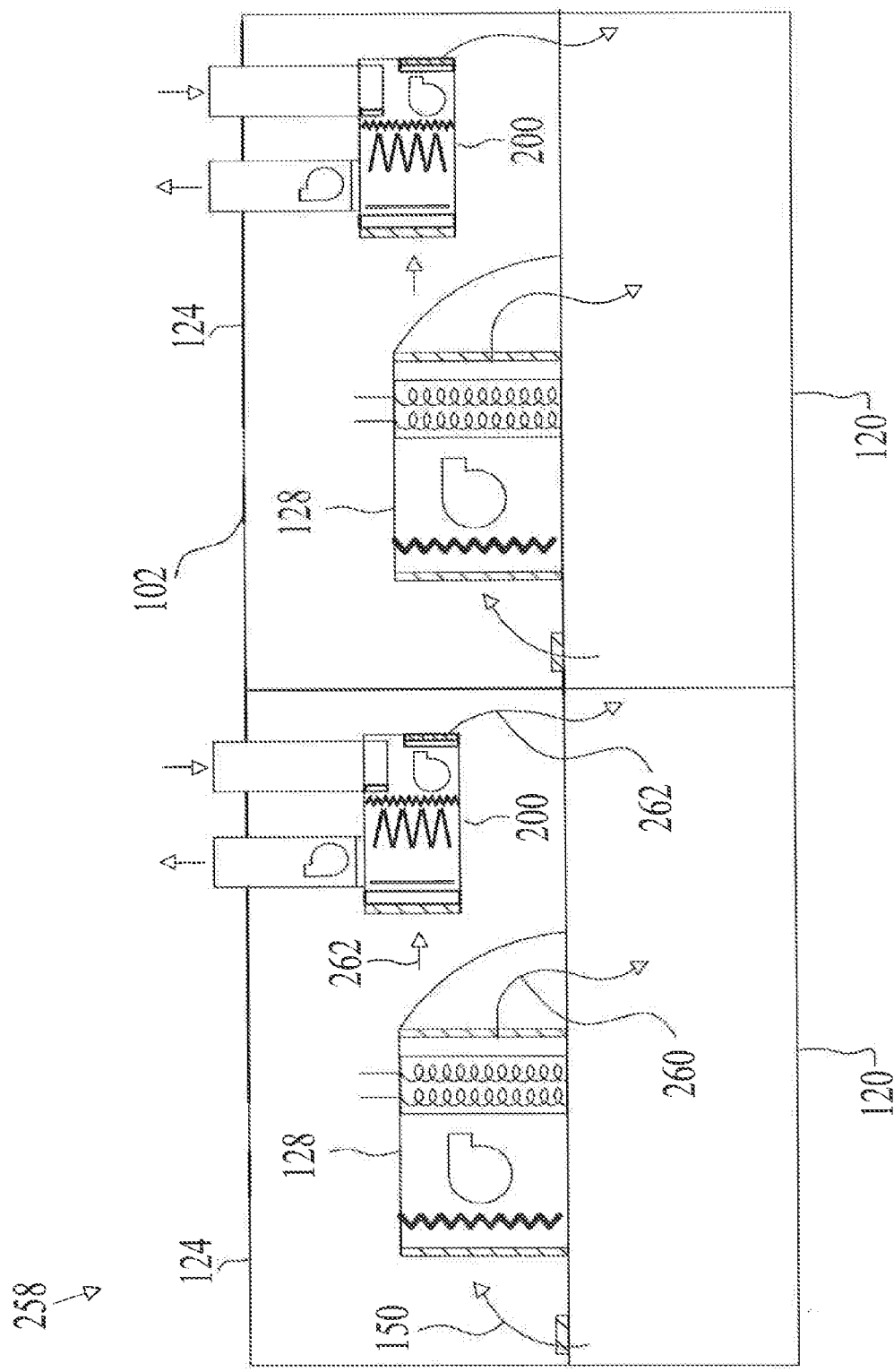
FIG. 5 is a simplified schematic illustration of another system for conditioning air in an enclosed environment according to some embodiments of the present disclosure.

In FIG. 5, a system 258 for conditioning air in the enclosed environment 102 is shown. As seen in FIG. 5, the return air 150 initially flows into the fan-coil unit 128. A portion 260 of the conditioned air exiting the fan-coil unit 128 may be directed into the indoor space 120 and a portion 262 of the conditioned air may flow into the scrubber 200. The scrubbed air exiting the scrubber 200 may be directed into the indoor space 120.

In some embodiments the fan-coil unit 128 may be placed in the air plenum 124, as seen in FIGS. 1-5. In other embodiments the fan-coil unit 128 may be placed within the indoor space 120 on a floor 270 (FIG. 6) or in proximity thereto, near a wall 274 or on a ceiling 276 or in proximity thereto. The scrubber 200 may be placed in the air plenum 124, as seen in FIGS. 1-5. In other embodiments the fan-coil unit 128 may be placed within the indoor space 120 under the floor 270 or in proximity thereto, near the wall 274 or in proximity thereto or on the ceiling 276 or in proximity thereto.

Figure 6:
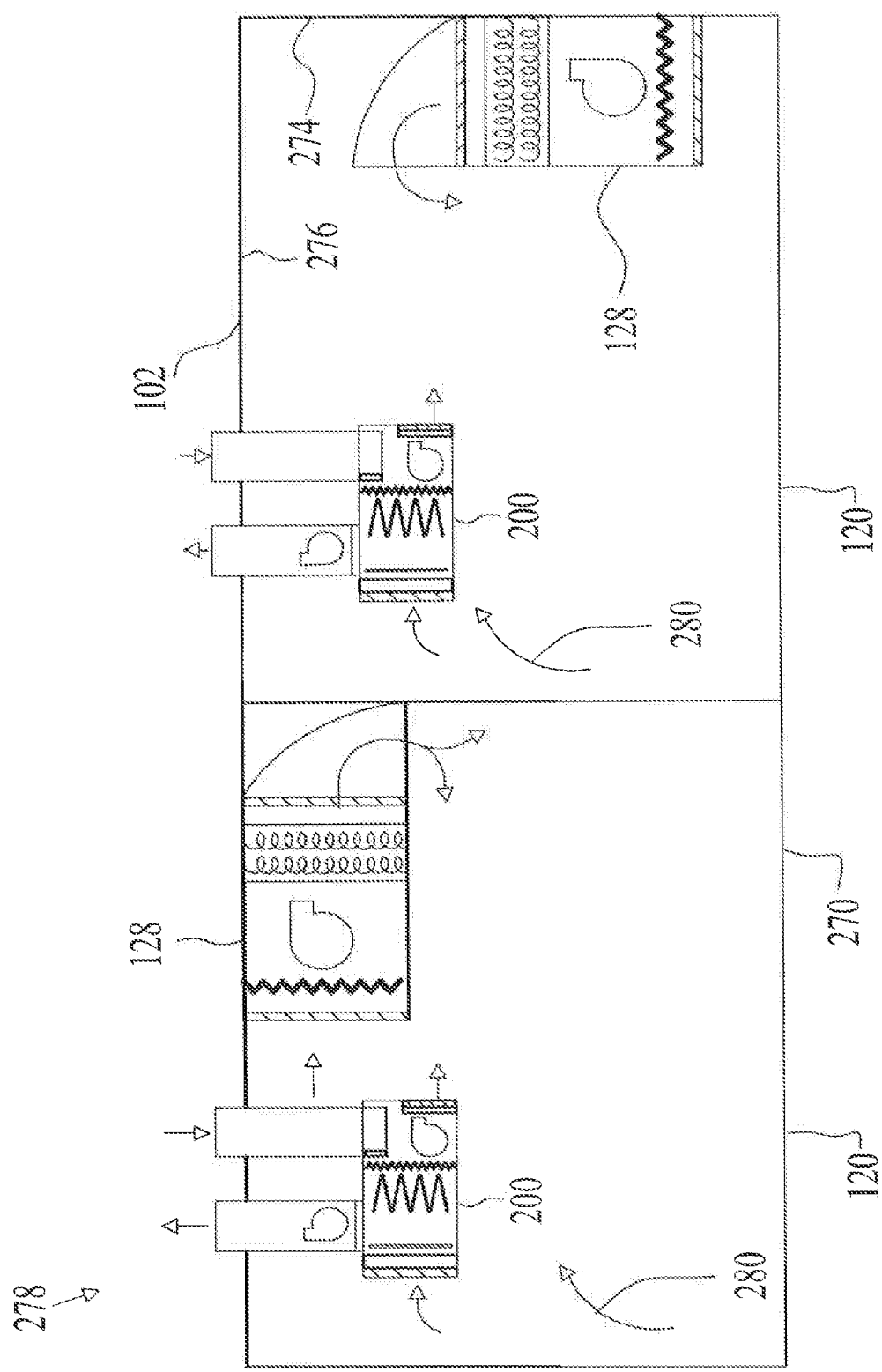
FIG. 6 is a simplified schematic illustration of yet another system for conditioning air in an enclosed environment according to some embodiments of the present disclosure.

In FIG. 6 a system 278 for conditioning air in the enclosed environment 102 is shown. In the left side indoor space 120 the fan-coil unit 128 is shown to be mounted horizontally beneath the ceiling 276 and in the right side indoor space 120 the fan-coil unit 128 is shown to be mounted vertically on the wall 274. The indoor air, illustrated by arrows 280, circulates within the indoor space 120. A portion of the indoor air 280 may enter the scrubber 200. The scrubber 200 may be placed in any suitable location within the indoor space 120, such as in proximity to the ceiling 276, for example.

The scrubbed air exits the scrubber 200 into the indoor space 120 for further circulation thereof.

Figure 7:
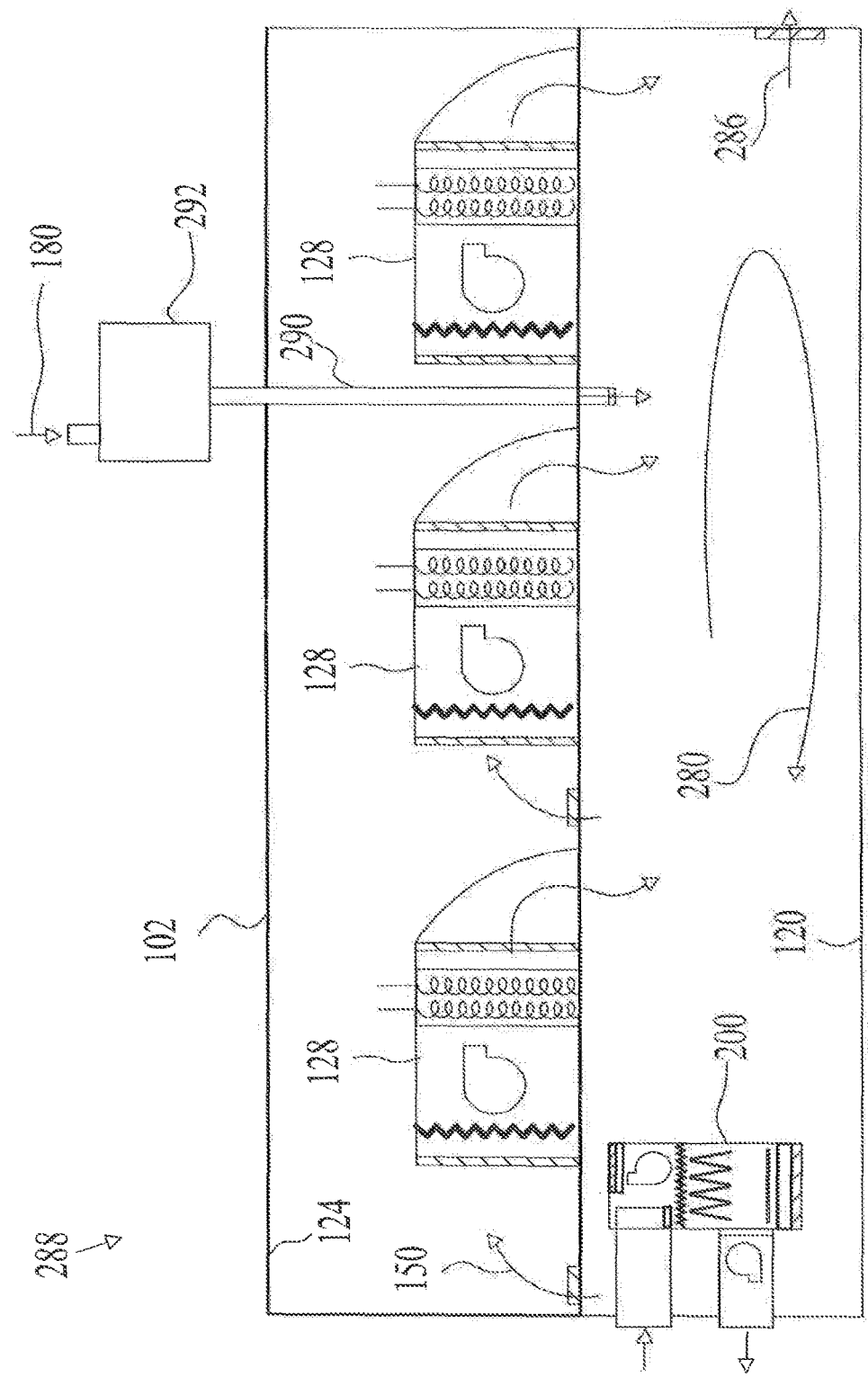
FIG. 7 is a simplified schematic illustration of still another system for conditioning air in an enclosed environment according to some embodiments of the present disclosure.

In FIG. 7, a system 288 for conditioning air in the enclosed environment 102 is shown. As seen in FIG. 7, the enclosed environment 102 may comprise a single indoor space 120. A plurality of fan-coil units 128 may be provided for conditioning the return air 150 and circulating the conditioned air back into the indoor space 120. The plurality of fan-coil units 128 may be placed in the air plenum 124, as shown in FIG. 7, or in any suitable location within the indoor space 120, as described in reference to FIG. 6.

A single scrubber 200 may be provided to scrub the indoor air, as shown in FIG. 7, or a plurality of scrubbers 200 may be provided. In some embodiments each scrubber 200 may be associated with a specific fan-coil unit 128. In some embodiments the plurality of scrubbers 200 may be placed within the indoor space 120 and may not be associated with a specific fan-coil unit 128.

The scrubber 200 may be placed in any suitable location within the enclosed environment 102 as described in reference to FIG. 6. In FIG. 7 the scrubber is placed within the indoor space 120.

In some embodiments, as shown in FIG. 7, a portion of the indoor air 280 may be exhausted out of the enclosed environment via exhaust ports 286. Fresh, outdoor air 180 may be introduced into the indoor space 120 or any other suitable location, via a duct 290. In some embodiments the fresh, outdoor air 180 may be cooled or heated prior to entrance into the enclosed environment by a fresh air, pre-conditioning unit 292, thereby reducing a degree of cooling or heating required by the fan-coil units 128.

Scrubbing the indoor air 280 within the scrubber 200 allows for reducing the volume of fresh, outdoor air 180 required for maintaining good air quality within the indoor space 120. Accordingly, the energy required to condition the outdoor air 180 is reduced. Additionally, introduction of potential pollutants and contaminants from the outdoor air 180 into the enclosed environment 102 is reduced.

In some embodiments, fresh, outdoor air 180 may not be introduced into the enclosed environment 102 of FIG. 7.

Figure 8:
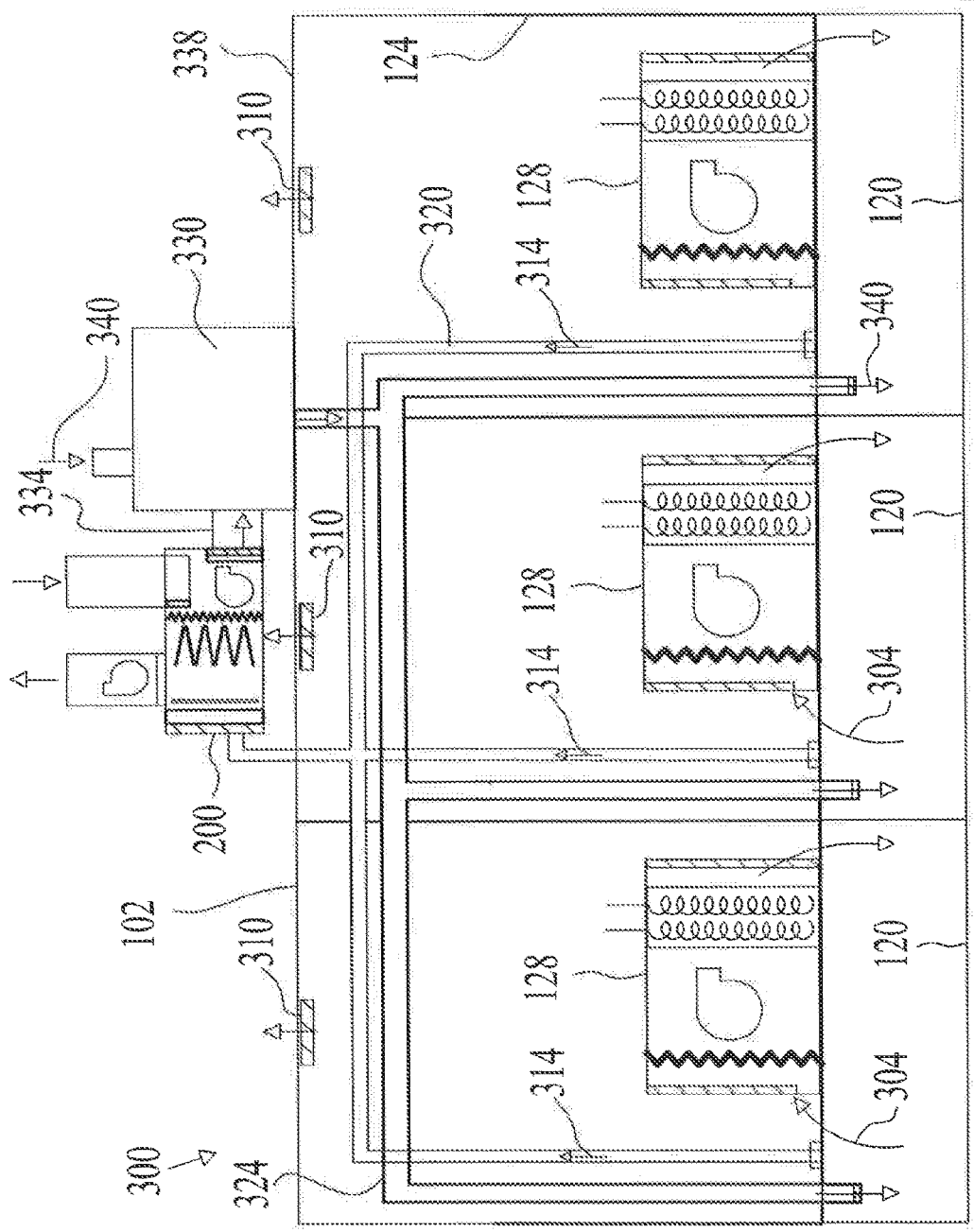
FIG. 8 is a simplified schematic illustration of yet another system for conditioning air in an enclosed environment according to some embodiments of the present disclosure.

In FIG. 8, a system 300 for conditioning air in the enclosed environment 102 is shown. As seen in FIG. 8, the enclosed environment 102 comprises a plurality of indoor spaces 120 each associated with its fan-coil unit 128. In a non-limiting example shown in FIG. 8, the fan-coil units 128 are set above the ceiling, within or without the air plenum 124. The fan-coil units 128 may have a common supply of a refrigerant fluid supplied from a shared chiller or heat pump (not shown). In accordance with some embodiments, the refrigerant fluid may comprise chilled water or may be supplied by a variable refrigerant flow (VRF) system. A portion of return air 304 may flow out of each indoor space 120 directly to the fan-coil unit or into the air plenum 124. This portion of the return air 304 may flow into the fan-coil unit 128 for conditioning thereof and circulation into the indoor space 120. Some of the return air 304 may be exhausted out of the enclosed environment 102, such as via exhaust ports 310 located in each of the air plenums 124 or any other suitable location.

Another portion of return air 314 may be directed to flow into a shared scrubber 200, via conduits 320 or without conduits by any other suitable manner. In some embodiments the conduits 320 may be installed specifically for flow into the scrubber 200. In other embodiments existing conduits or ducts in the enclosed environment (e.g. building) may be used, such as standard ducts provided for ventilation or elevators or for exhaust such as smoke exhaust.

Scrubbed air, exiting the scrubber 200, may be introduced back into the indoor spaces 120 via conduits 324 or in any other suitable manner. In some embodiments conduits 324 may comprise existing indoor air conduits or ducts, such as ducts 184 of FIG. 1. The scrubbed air may initially flow from the scrubber 200 into a fresh air pre-conditioning unit 330, such as the fresh air pre-conditioning unit 292 shown in FIG. 7. The scrubbed air may be cooled or heated within the fresh air pre-conditioning unit 330 prior to flow in conduits 324, thereby reducing a degree of cooling or heating required by the fan-coil units 128. The scrubbed air may flow from the scrubber 200 into the fresh air preconditioning unit 330 via a conduit 334 or by any other suitable means.

In some embodiments a plurality of scrubbers 200 may be provided.

The scrubber 200 may be placed in a suitable location, such as on a roof 338 of the enclosed environment 102 or out of the enclosed environment 102 or within the enclosed environment 102 such as in a mechanical room or any other location.

Scrubbing the return air 314 within the scrubber 200 allows for reducing the volume of fresh, outdoor air 340 required for maintaining good air quality within the indoor space 120. In some embodiments, such as wherein exhaust ports 310 are not provided, introduction of fresh, outdoor air 340 may be eliminated.

Figure 9A:
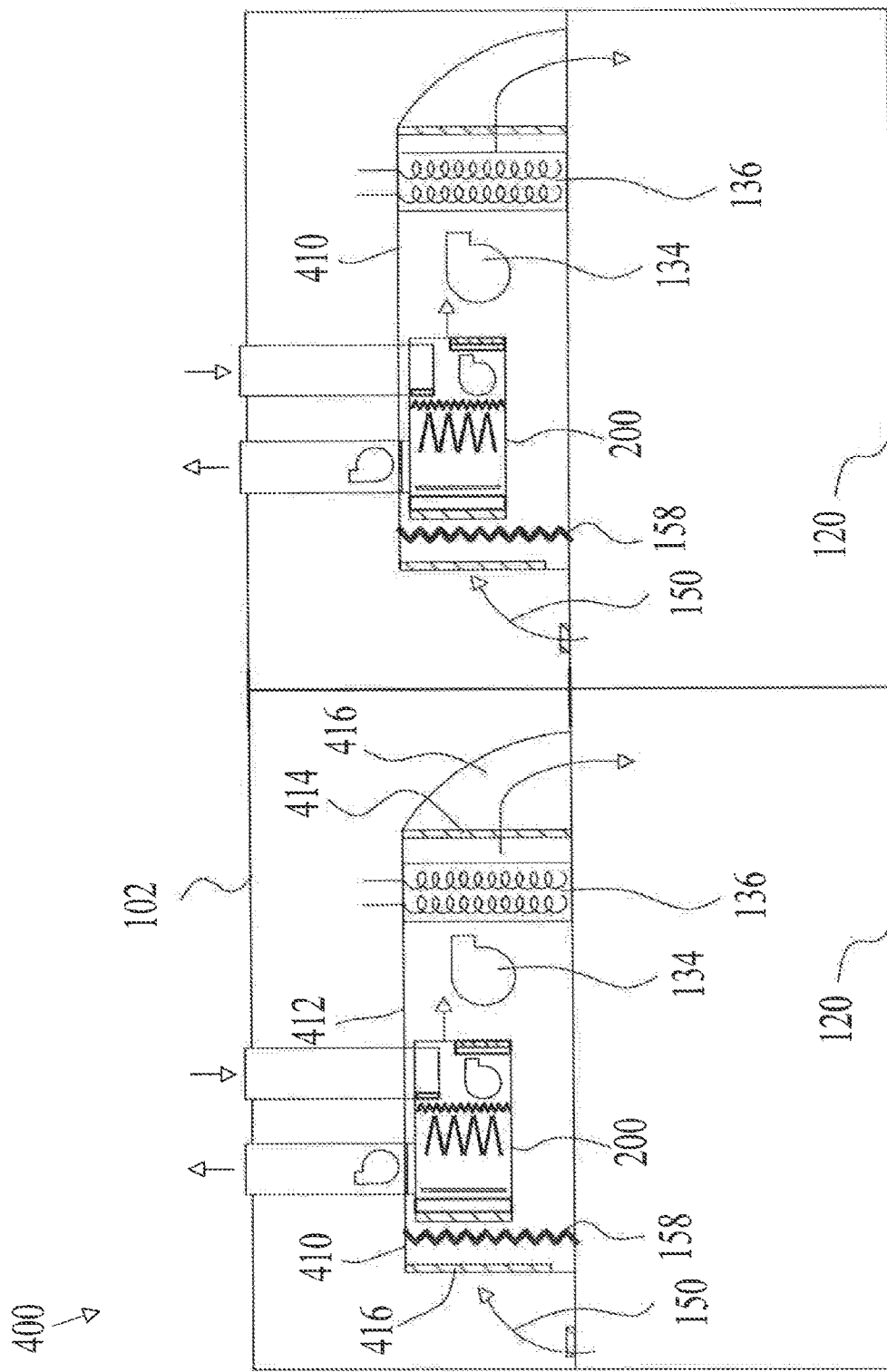
Figure 9B:
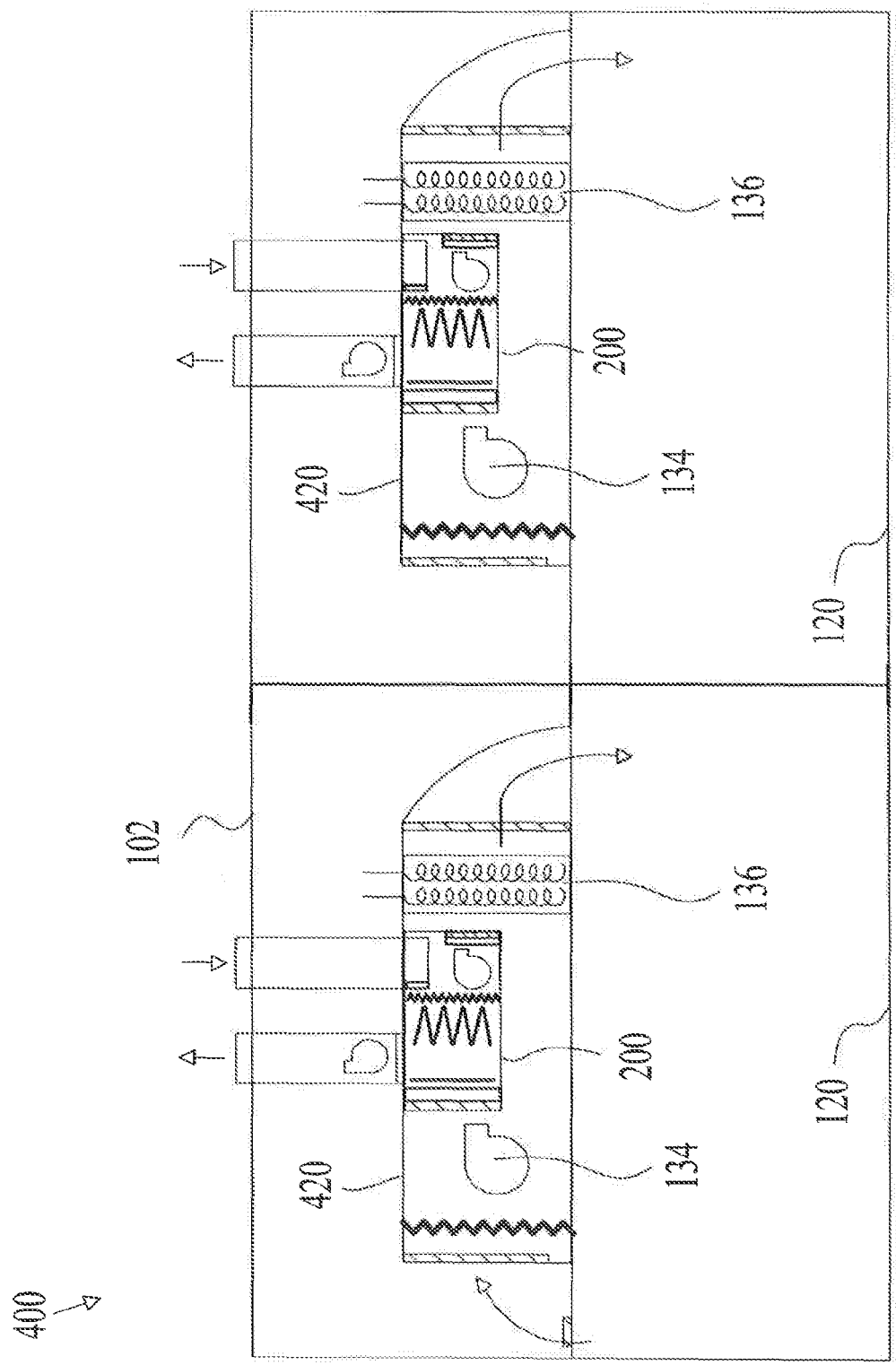

In FIG. 9A-9E a system 400 for conditioning air in the enclosed environment 102 is shown. As seen in FIG. 9A an integrated fan-coil unit 410 comprises a housing or mechanical frame 412 that is connecting or otherwise shared by the scrubber 200 and the fan-coil unit 128. Return air 150 may enter the integrated unit 410 via an entry port 416 and may be initially filtered by filter 158. Thereafter, a portion of the return air 150 may be scrubbed within the scrubber 200 and a remaining portion of return air may bypass the scrubber 200. The scrubbed air and the bypassed air are urged by the fan 134 to flow to the coils 136 to be cooled or heated thereby. The conditioned air may exit the integrated unit 410 via an exit port 414 and duct 416 so as to be circulated into the indoor space 120.

In the embodiment shown in FIG. 9A, the scrubber 200 is placed prior to the fan 134 and coils 136, in respect to the direction of the return air flow. In the embodiment shown in FIG. 9B, an integrated unit 420 is provided and the scrubber 200 is placed intermediate the fan 134 and coils 136. In the embodiment shown in FIG. 9C an integrated unit 430 is provided and the scrubber 200 is placed after the fan 134 and coils 136, in respect to the direction of the return air flow.

Figure 9D:
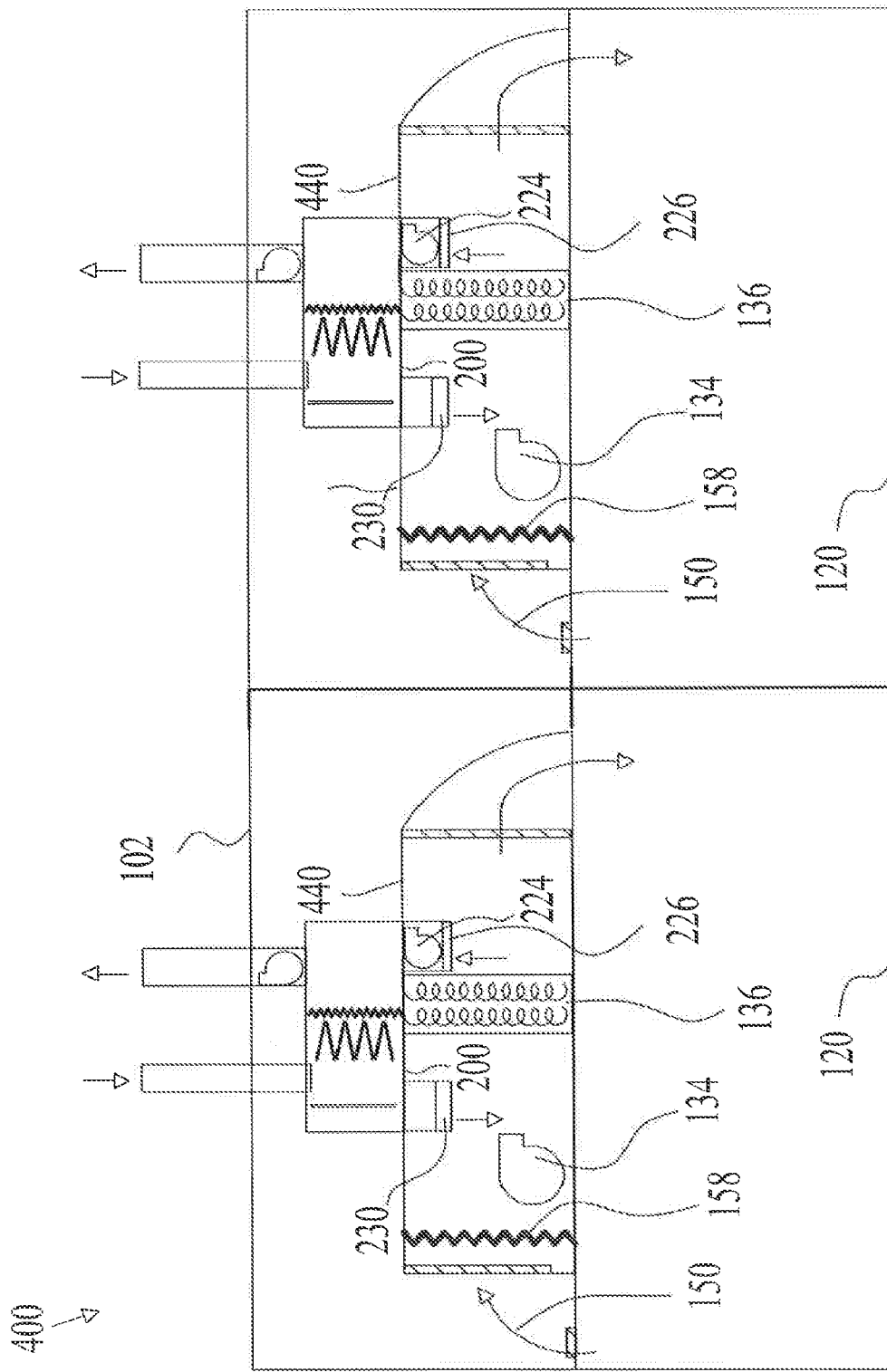

In the embodiment shown in FIG. 9D, an integrated unit 440 is provided. The entry port 226 to the scrubber 200 is provided following the fan 134 and the coils 136. The exit port 230 is placed intermediate the fan 134 and coils 136. Return air 150 flowing into the integrated unit 440 may flow through filter 158. The fan 134 urges the return air 150 to flow to the coils 136 for cooling or heating thereby. A portion of the cooled or heated air may bypass the scrubber 200 and flow out of the integrated unit 440. A remaining portion of the cooled or heated air may be urged by scrubber fan 224 to enter the entry port 226 into the scrubber 200. The scrubbed air may exit the scrubber via exit port 230 and may be cooled or heated again by the coils 136 prior to flowing out of the integrated unit 440.

Figure 9E:
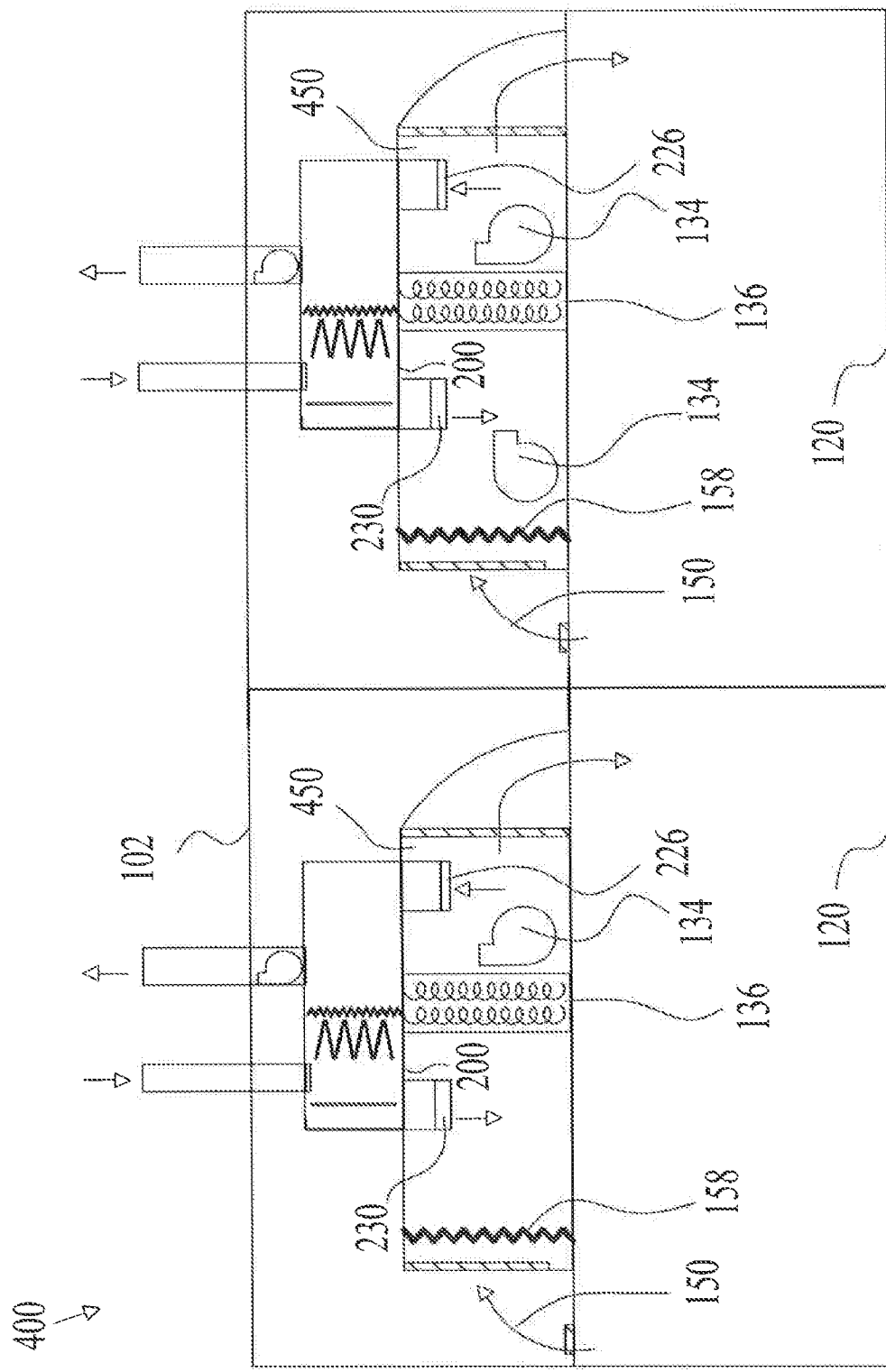

In the embodiment shown in FIG. 9E, an integrated unit 450 is provided. Here the entry port 226 to the scrubber 200 is positioned following the coils 136. The fan 134 is positioned intermediate the coils 136 and the entry port 226. The exit port 230 is placed prior the coils 136. Return air 150 flowing into the integrated unit 450 may flow through filter 158. The fan 134 urges the return air 150 to flow to the coils 136 for cooling or heating thereby. A portion of the cooled or heated air may bypass the scrubber 200 and flow out of the integrated unit 450. A remaining portion of the cooled or heated air may be urged by fan 134 to enter the entry port 226 into the scrubber 200. The fan 134 of the fan-coil unit 128 may be sufficient for urging the cooled or heated air to flow into the scrubber 200 and the scrubber fan may be eliminated. The scrubbed air may exit the scrubber via exit port 230 and may be cooled or heated again by the coils 136 prior to flowing out of the integrated unit 450.

The integrated units 410, 420, 430, 440 and 450 may be placed within the air plenum 124, as shown in FIGS. 9A-9E, or within the indoor space 120 or any other suitable location.

Use of an integrated unit, such as shown in FIGS. 9A-9E, simplifies the installation or connection of the scrubber 200 and fan-coil unit 128. Additionally, in some embodiments, components of the fan-coil unit 128 may be used for the scrubber 200. For example the fan 134 may be used to aid in directing air into the scrubber 200, and may even eliminate the need for a separate scrubber fan, as seen in FIG. 9E. Moreover, the purge gas 240 may be heated by heating coil 140 or other heating means within the fan-coil unit 128.

As described in reference to FIGS. 1-9E, the purge gas 240 may be heated prior to flow into the scrubber 200. Additionally, the purge gas 240 may be heated within the scrubber 200, such as in entry conduit 244. The purge gas 240 may be heated in any suitable manner. For example, the purge gas 240 may be heated by an electric heating coil, a coil or radiator with heated fluid supplied from a central heating system in the enclosed environment 102, solar heat, such as solar heat provided to the enclosed environment 102, an appropriately sized furnace burning gas or other fuel (not shown) for heating the purge gas 240. Some additional exemplary methods are described in reference to FIGS. 10A and 10B.

In FIG. 10A, a system 500 for conditioning air in the enclosed environment 102 is shown. In accordance with some embodiments, a warm fluid may be used to heat the purge gas 240. For example, a fluid coil 510, such as a copper or other metal tube, is placed at the entry conduit 244 and the coil 510 is supplied with warm fluid. In some embodiments, the warm fluid may be heated within a heating plant or boiler (not shown) provided specifically for heating the purge gas 240. In some embodiments, the warm fluid may be heated by an existing supply of warm fluid provided in a standard enclosed environment 102, such as a building's hot water supply or the warm fluid provided to the heating coils 140 of the fan-coil unit 128.

In FIG. 10B, a system 600 for conditioning air in the enclosed environment 102 is shown where, according to some embodiments, a heat pump 610 may be utilized to heat the purge gas 240. Typically, the heat pump 610 comprises a condenser side, or a hot side 620. The purge gas 240 may directly contact the hot side 620 and may be heated thereby. Alternatively, a heating element 624 may be heated by the hot side 620 and the purge gas 240 may be heated by the heating element 624. Additionally, the hot side 620 may be used to directly heat the adsorbent material in the scrubber 200. Use of a heat pump 610 may be advantageous, since to operate the heat pump 610 less power is required than other heating means, such as electric heating, for example.

In some embodiments, an evaporator side or a cold side 630 of the heat pump 610 may be used to remove heat from the return air 150 flowing within the air plenum 124, or the air flowing through the fan coil unit, or any other air within the indoor space 120. The now cooled air directly or indirectly lessens the cooling power required by the fan-coil unit 128.

Figure 11A:
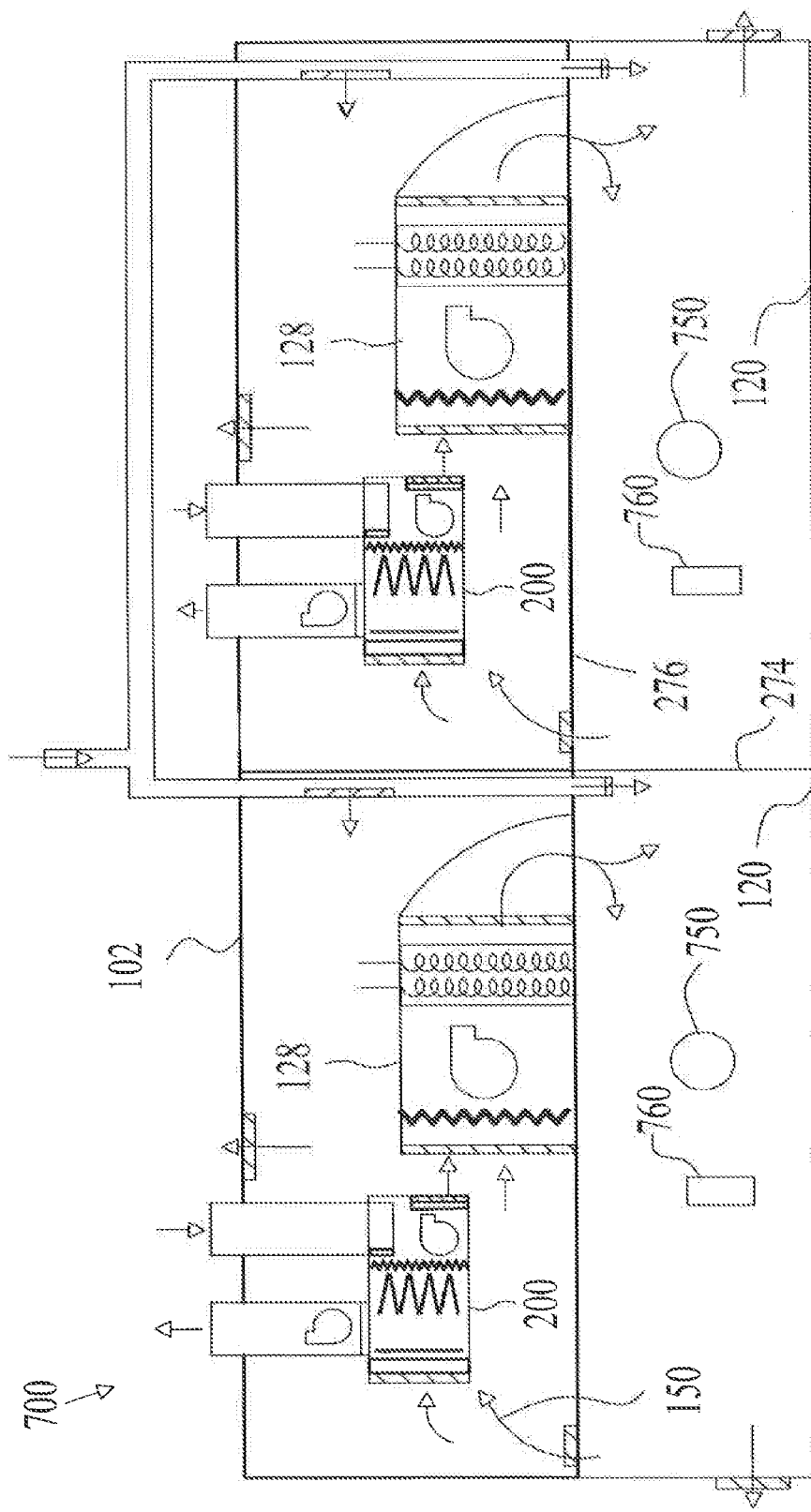
Figure 11B:
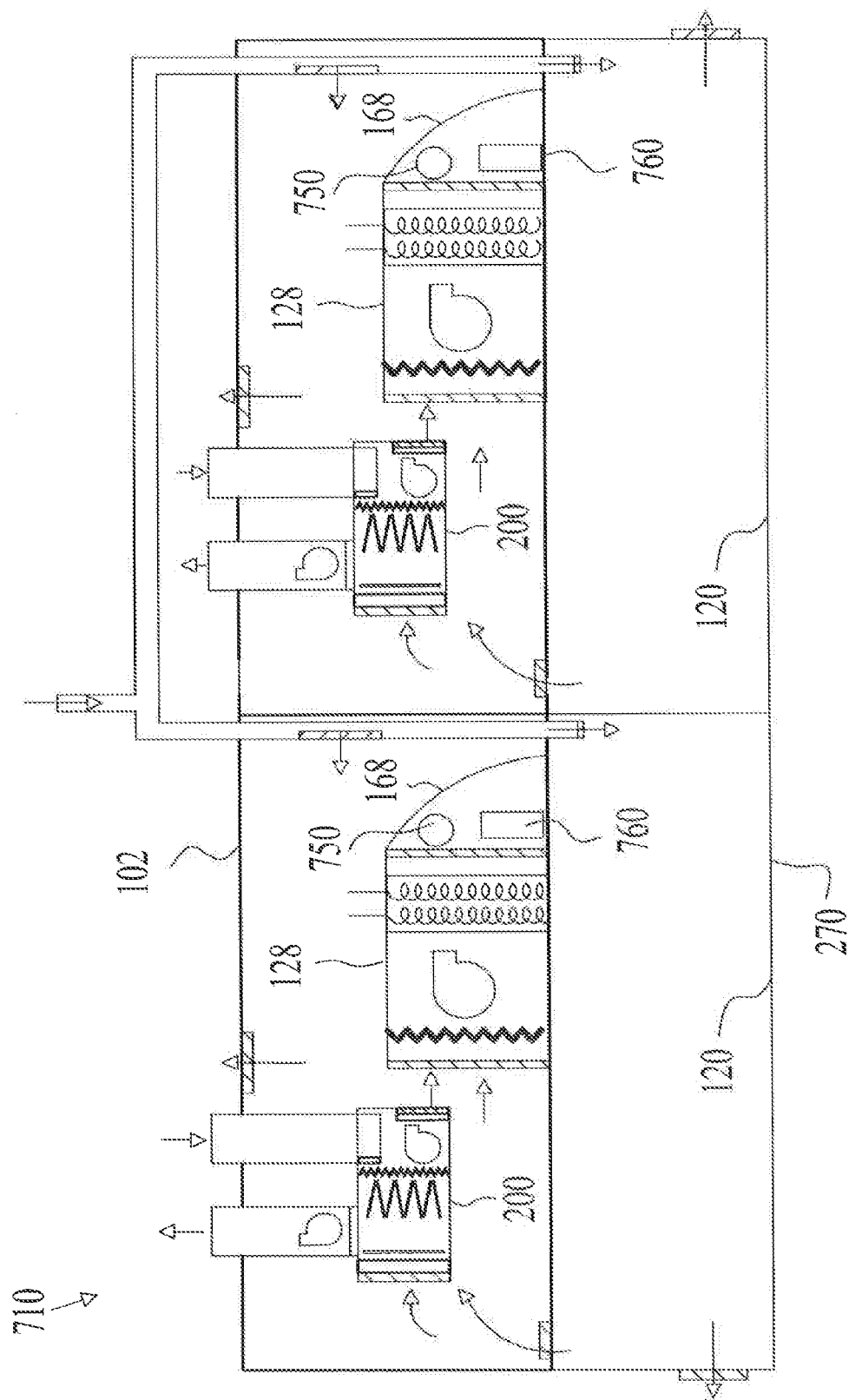
Figure 11C:
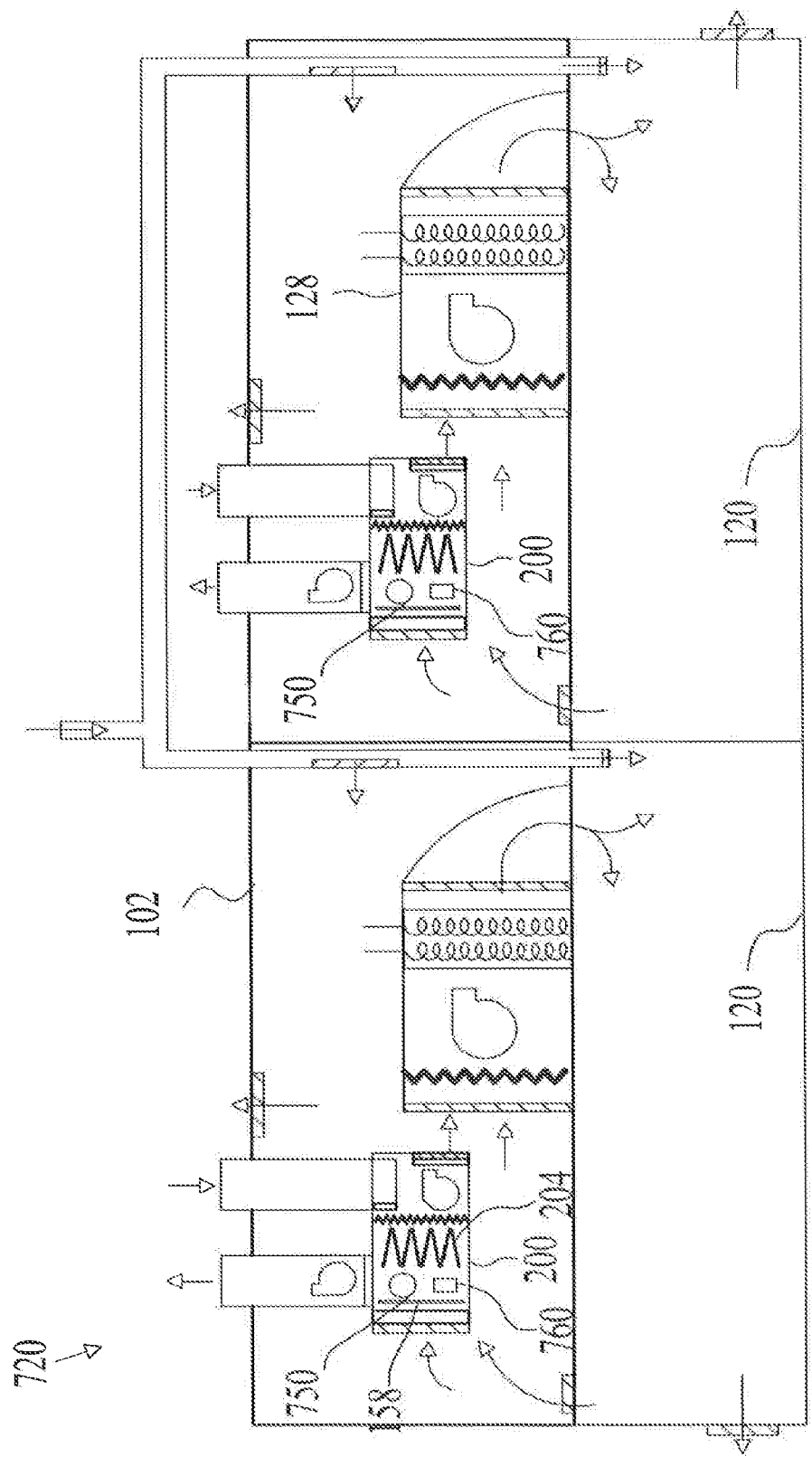

In FIGS. 11A-11D, respective systems 700, 710, 720 and 730 for conditioning air in the enclosed environment 102 according to some embodiments are shown. As seen in FIGS. 11A-11C, the systems 700, 710, 720 are similar to the system 100 of FIG. 1.

In accordance with some embodiments, an air ionizer 750 or air purifier may be provided at any suitable location within the enclosed environment 102 to enhance the air quality therewithin. The air ionizer 750 typically emits electrically charged ions that clean impurities from the air within the enclosed environment 102. The air ionizer 750 may be provided to otherwise improve air quality within the enclosed environment 102.

The air ionizer 750 may be placed at any suitable location. For example, as seen in FIG. 11A, the air ionizer 750 is placed in the center of the indoor space 120. Additionally, the air ionizer 750 may be mounted to the wall 274 or ceiling 276 of the indoor space 120 or any other suitable location within the enclosed environment 102.

As seen in FIG. 11B, the air ionizer 750 may be associated with the fan-coil unit 128, and may be placed in the duct 168, for example. Turning to FIG. 11C, it is seen that the air ionizer 750 may be placed within the scrubber 200 at any suitable location, such as intermediate the filter 158 and the $CO_2$ scrubber 204, for example.

In accordance with some embodiments, a microorganism removal device 760 may be provided for removal of microorganisms including, inter alia, bacteria, viruses, molds and fungi, from the enclosed environment 102 in any suitable manner. In a non-limiting example the removal device 760 may comprise an ultraviolet anti-microbial device. The removal device 760 may include an air filter with a media formed of foam, paper, fiberglass, oxides, catalysts, or any other suitable material. Additionally the removal device 760 may remove the microorganisms using an ozone source, a source of radiation, ion or plasma generators, chemical catalysts, a membrane and/or a heater.

The removal device 760 may be placed at any suitable location. For example, as seen in FIG. 11A, the removal device 760 is placed in the center of the indoor space 120. Additionally, the removal device 760 may be mounted to the wall 274 or ceiling 276 of the indoor space 120 or any other suitable location within the enclosed environment 102.

As seen in FIG. 11B, the removal device 760 may be associated with the fan-coil unit 128, and may be placed in duct 168, for example. Turning to FIG. 11C, it is seen that the removal device 760 may be placed within the scrubber 200 at any suitable location, such as intermediate the filter 158 and the $CO_2$ scrubber 204, for example.

It is noted that additional contaminant removal devices may be provided within the systems of FIGS. 1-11D. For example, a device for removing dust in any suitable manner may be provided or a plasma generator, or chemical catalysts may be provided.

It is noted that the air ionizer 750 and the microorganism removal device 760 may be placed in any one of the systems shown in FIGS. 1-10B.

In FIG. 11D, the system 730 for conditioning air in an enclosed environment 802 is shown. The enclosed environment 802 may be similar to enclosed environment 102 of FIGS. 1-11C. As seen in FIG. 11D, the system 730, according to some embodiments, may comprise a conventional air handling unit 810 for conditioning the circulated indoor air of the enclosed environment 802 and ducts 812 for directing the indoor air flow within the system 800. Return air 814 may exit the enclosed environment 802, which may be partially exhausted as exhaust air 818, via exhaust ducts 820, into the ambient, and may be partially reintroduced into the enclosed environment 802. A portion of the return air 814 may be introduced into the scrubber 800 prior to flow back into the enclosed environment 802. Fresh, outdoor air 830 may be introduced into the system 730 via ducts 834.

In accordance with some embodiments, the air ionizer 750 may be provided at any suitable location, such as within the enclosed environment 802 or at an entrance thereto.

The microorganism removal device 760 may be provided at any suitable location, such as within the enclosed environment 802, or at an entrance thereto or exit therefrom. Additionally, the removal device 760 may be placed before entry or after the exit to the scrubber 200.

Moreover the air ionizer 750 or removal device 760 may be placed within the scrubber 200, such as the scrubber shown in FIG. 11C.

It is noted in reference to FIGS. 1-11D, that any other suitable means besides dampers, such as valves, fans or shutters, may be used to control the volume of air entering and/or exiting the fan-coil unit 128 or the scrubber 200.

In some embodiments of the systems shown in FIGS. 1-11D, a single or plurality of sensors (not shown) may be provided to detect levels of one or more contaminants, substances, gases (such as $CO_2$ and other gases), fumes, vapors, (such as VOCs) and/or any combination thereof. The sensors may be placed in any suitable location within the enclosed environment 102 or in proximity thereto. Upon detection of a particular concentration of such contaminants, substances, gases, etc., the sensor(s) may be configured to generate output data that can be transmitted to a control system (not shown) for processing thereof.

The control system may be operative to control any one or more of: the duration of time the scrub cycle and the purge cycle, the volume of air flowing into the scrubber for scrubbing thereof, the volume of purge gas flowing into the scrubber for regeneration of the scrubber, and switching of the scrubber from the scrub cycle to the purge cycle and vice versa.

In some embodiments, the control system may be designed to control the duration and air volume during the scrub cycle and the purge cycle and switching of the scrubber from the scrub cycle to the purge cycle and vice versa, according to a preset schedule, or by sensing a predetermined level of the contaminants by the sensors and accordingly operating the scrub cycle or purge cycle, or by determining an occupancy level of the indoor space 120 and, accordingly, operating the scrub cycle or purge cycle, for example. The duration or volume during the scrub cycle or purge cycle and switching therebetween may be controlled by a manual trigger or by externally signaled commands or any other suitable means.

In some embodiments, the control system may be designed to activate the scrubber in response to actual contaminant levels, occupancy, or preset schedules.

It is noted that the ducts disclosed throughout the application may comprise conduits, pipes or any suitable means for directing air to flow therethrough.

Example embodiments of the methods and components of the current subject matter have been described herein. As noted elsewhere, these example embodiments have been described for illustrative purposes only, and are not limiting. Other embodiments are possible and are covered by the current subject matter. Such embodiments will be apparent to persons skilled in the relevant art(s) based on the teachings contained herein. Moreover, a feature(s) from one embodiment(s) may be used in combination or in place of a feature(s) of another embodiment(s). Thus, the breadth and scope of the current subject matter should not be limited by any of the above-described exemplary embodiments, but should be defined only in accordance with the following claims and their equivalents.

What is claimed is:

1. An air treatment system for conditioning air in a building, comprising:
a fan-coil unit arranged adjacent to or within the indoor space;
a scrubber configured during a scrub cycle to scrub air from an indoor space of the building, and being positioned within or adjacent the indoor space, the scrubber including:
one or more adsorbent materials arranged therein to adsorb at least one predetermined gas from the air of the indoor space during the scrub cycle,
a source of outdoor air, and
an exhaust,
wherein the scrubber is configured:
during a purge cycle to direct a purging air flow, received via the source of outdoor air, over and/or through the adsorbent materials to purge at least a portion of the at least one predetermined gas adsorbed by the adsorbent materials during the scrub cycle from the adsorbent materials and thereafter exhausting the flow via the exhaust, and
during a scrub cycle to supply scrubbed air to the fan-coil unit.

2. A system according to claim 1, wherein the scrubber is configured to supply scrubbed air exiting the scrubber to the indoor space.

3. A method for conditioning air in a building, comprising:
circulating indoor air of an indoor space via a fan-coil unit;
optionally heating or cooling the circulated indoor air;
scrubbing the indoor air during a scrub cycle using a scrubber placed within or adjacent to the indoor space, the scrubber comprising:
one or more adsorbent materials arranged therein to adsorb at least one predetermined gas from the air of the indoor space during the scrub cycle;
a source of outdoor air, and an outdoor exhaust;
flowing a purging air flow received via the source of outdoor air over and/or through the one or more adsorbent materials so as to purge the adsorbent materials of at least a portion of the at least one gas adsorbed by the one or more adsorbent materials; and
thereafter exhausting the purging air flow via the exhaust.

4. The method of claim 3, wherein the fan-coil unit is supplied refrigerant or heating fluid from a variable refrigerant flow (VRF) system.

5. The method of claim 3, wherein the fan-coil unit is supplied chilled or heated water from a central chiller or boiler.

6. The method of claim 3, wherein the scrubber further comprises at least one of a damper and a fan, and wherein the method further comprises switching the scrubber from the scrub cycle to the purge cycle using the at least one of the fan and the damper.

7. The method of claim 3, further comprising performing the switching according to at least one of: a preset schedule, a predetermined level of the predetermined gas, the enclosed space occupancy level, a manual trigger, a signaled command and an externally signaled command.

8. A system for conditioning air in a building comprising:
a plurality of indoor spaces within the building;
a plurality of fan-coil units arranged adjacent to or within the plurality of indoor spaces and additionally configured to at least one of heat and cool the air of the plurality of indoor spaces; and
a scrubber arranged within the building, the scrubber configured during a scrub cycle for scrubbing of indoor air from the plurality of indoor spaces, the scrubber including:
one or more adsorbent materials arranged therein to adsorb at least one predetermined gas from the indoor air during the scrub cycle;
a source of outdoor air, and
an exhaust,
wherein the scrubber is configured during a purge cycle to direct a purging air flow received from the source of outdoor air over and/or through the adsorbent materials to purge at least a portion of the at least one predetermined gas adsorbed by the adsorbent materials during the scrub cycle from the adsorbent materials and thereafter exhausting the flow via the exhaust.

9. The system of claim 8 wherein the fan-coil unit is supplied refrigerant or heating fluid from a variable refrigerant flow (VRF) system.

10. The system of claim 8 wherein more than one of the plurality of fan-coil units is supplied refrigerant or heating fluid from a common variable refrigerant flow (VRF) system.

11. The system of claim 8 wherein the fan-coil unit is supplied chilled or heated water from a central chiller or boiler.

12. The system of claim 8 wherein scrubbed air exiting the scrubber is directed to the plurality of indoor spaces via conduits.

13. The system of claim 8 wherein indoor air is directed to the scrubber from the plurality of indoor spaces via conduits.

14. A system of claim 13 wherein the conduits are installed and configured for directing the indoor air from the plurality of indoor spaces to the scrubber.

15. A system of claim 13 wherein the conduits are pre-existing in the building.

16. A system of claim 15 wherein the pre-existing conduits are configured for ventilation, elevators, exhaust, or smoke exhaust.

17. A system of claim 8 and comprising a pre-conditioning unit configured to at least heat or cool outside air or scrubbed air exiting the scrubber and direct the preconditioned air to the plurality of indoor spaces.

18. A system of claim 17 wherein the pre-conditioned air is directed to the plurality of indoor spaces via conduits.

19. The system of claim 8 where the predetermined gas is selected from the group consisting of: carbon dioxide, volatile organic compounds, sulfur oxides, radon, nitrous oxides and carbon monoxide.

* * * * *